United States Patent
Scheefers et al.

(10) Patent No.: US 9,766,243 B2
(45) Date of Patent: Sep. 19, 2017

(54) TEST KIT (COMBINED QUICK TEST) FOR THE SYNCHRONOUS PROOF OF BIOMARKERS IN FAECES FOR DETECTING OF PATHOLOGICAL CHANGES IN THE GASTROINTESTINAL TRACT, PARTICULARLY IN THE INTESTINE

(71) Applicant: SCHEBO BIOTECH AG, Giessen (DE)

(72) Inventors: Hans Scheefers, Wettenberg (DE); Ursula Scheefers-Borchel, Wettenberg (DE)

(73) Assignee: SCHEBO BIOTECH AG, Giessen (DE)

( * ) Notice: Subject to any disclaimer, the term of this patent is extended or adjusted under 35 U.S.C. 154(b) by 23 days.

(21) Appl. No.: 14/413,743

(22) PCT Filed: Jul. 9, 2013

(86) PCT No.: PCT/DE2013/000380
§ 371 (c)(1),
(2) Date: Jan. 9, 2015

(87) PCT Pub. No.: WO2014/008884
PCT Pub. Date: Jan. 16, 2014

(65) Prior Publication Data
US 2015/0219658 A1    Aug. 6, 2015

(30) Foreign Application Priority Data

Jul. 9, 2012    (DE) .................. 10 2012 013 888
Dec. 18, 2012    (DE) .................. 20 2012 012 084 U

(51) Int. Cl.
*G01N 33/574*    (2006.01)
*G01N 33/558*    (2006.01)
(Continued)

(52) U.S. Cl.
CPC ..... *G01N 33/57419* (2013.01); *G01N 33/558* (2013.01); *G01N 33/573* (2013.01);
(Continued)

(58) Field of Classification Search
CPC ........... G01N 33/57419; G01N 33/558; G01N 33/573; G01N 33/57446; G01N 33/726
See application file for complete search history.

(56) References Cited

U.S. PATENT DOCUMENTS 4,333,734 A    6/1982 Fleisher
4,376,110 A    3/1983 David et al.
(Continued)

FOREIGN PATENT DOCUMENTS

DE    10205709    8/2003
EP    0810436    2/1990
(Continued)

OTHER PUBLICATIONS

PKM2 antibody, www.biorbyt.com/pkm2-antibody-30, accessed Feb. 24, 2017.*

(Continued)

*Primary Examiner* — Melanie Y Brown
(74) *Attorney, Agent, or Firm* — Mayer & Williams, PC; Stuart H. Mayer

(57) ABSTRACT

The invention relates to a test kit for better carrying out a method for detecting biomarkers in human or animal stool, which can serve as an indication of a pathological, particularly a malignant event in the gastrointestinal tract (esophagus, stomach, small bowel, biliary tract, pancreas, and bowel).

The invention teaches a novel and more efficient methods, uses and embodiments of a combined rapid test. The combined rapid test cassette used for implementing the test kit and the optimally coordinated reagents thereof contains two (Continued)

lateral flow test strips for the synchronous—in the technical meaning—detection of the biomarkers M2-PK and the biomarker hemoglobin.

The test serves as a "dual filter" for diagnosing probands as part of a colon cancer screening program. The test is very cost-efficient and cuts costs in the health system by the examination at an early stage of colon cancer and the consequences thereof.

11 Claims, 7 Drawing Sheets

(51) Int. Cl.
 *G01N 33/573* (2006.01)
 *G01N 33/72* (2006.01)
(52) U.S. Cl.
 CPC ..... *G01N 33/57446* (2013.01); *G01N 33/726* (2013.01); *G01N 2333/91215* (2013.01)

(56) References Cited

U.S. PATENT DOCUMENTS

| | | | |
|---|---|---|---|
| 4,435,504 A | 3/1984 | Zuk | |
| 4,703,017 A | 10/1987 | Campbell et al. | |
| 4,855,240 A | 8/1989 | Rosenstein et al. | |
| 4,954,452 A | 9/1990 | Yost et al. | |
| 5,028,535 A | 7/1991 | Buechler et al. | |
| 5,075,078 A | 12/1991 | Osikowicz et al. | |
| 5,270,163 A | 12/1993 | Gold et al. | |
| 5,654,162 A | 8/1997 | Guire et al. | |
| 2002/0102623 A1* | 8/2002 | Erich | G01N 33/57484 435/7.23 |
| 2006/0134804 A1 | 6/2006 | Gao et al. | |
| 2008/0227208 A1* | 9/2008 | Yee | G01N 33/72 436/66 |
| 2009/0075311 A1* | 3/2009 | Karl | G01N 33/57419 435/15 |
| 2009/0087860 A1* | 4/2009 | Todd | C07K 16/3069 435/7.1 |

FOREIGN PATENT DOCUMENTS

| | | |
|---|---|---|
| EP | 0560411 A2 | 9/1993 |
| WO | 95-16207 | 6/1995 |
| WO | 01/21826 A2 | 3/2001 |
| WO | 0250546 | 6/2002 |
| WO | 03065003 | 8/2003 |
| WO | 03068398 | 8/2003 |
| WO | 03069343 | 8/2003 |
| WO | 2005/005991 A1 | 1/2005 |
| WO | 2007/071366 A1 | 6/2007 |

OTHER PUBLICATIONS

Shastri et al. Comparison of an Established Simple Office-Based Immunological FOBT with Fecal Tumor Pyruvate Kinase Type M2 for Colorectal Cancer Screening: Prospective Muticenter Study, American Journal of Gastroenterology, 2008, pp. 1496-1504.*
Carolin Tonus et al: "The faecal tumour M2-PK screening test for invasive & pre-invasive colorectal cancer: estimated specificity & results as a function of age for a study population of 4854 volunteers", Journal of Oncology, vol. 59, Jan. 1, 2009.
Trojan J et al: "A New Immunological Test Strip Device for the Rapid, Qualitative Detection of Faecal Occult Blood", Zeitschrift Fuer Gastroenterologie, Georg Thieme Verlag, DE, vol. 40, No. 11, Nov. 1, 2002 (Nov. 1, 2002), pp. 921-924.
J Blessing et al: "Verbesserte Darmkrebsvorsorge durch Stuhldiagnostik: M2-PK / Imnnunologischer Blutnachweis", Jan. 1, 2004.
J Blessing et al: "Untersuchungsprogramm", Apr. 17, 2012 (Apr. 17, 2012), pp. 1-428.
Uchida K et al: Il Immunochemical detection of human blood in feces, Clinica Chimica Acta, Elsevier BV, Amsterdam, NL, vol. 189, No. 3, Aug. 31, 1990 (Aug. 31, 1990), pp. 267-274.
Author unknown, "Tumour Markers in Gynecological Cancers—EGTM Recommendations" Anticancer Research 19:2785-2820 (1999).
Brenner et al., "Inter-test agreement and quantitative cross-validation of immunochromatographic fecal occult blood tests" Int. J. Cancer 127, 1643-1649 (2010).
Favennec L. et al., "Detection of occult blood in stools: comparison of three gaiac tests and a latex agglutination test" Ann. Biol. Clin. (1992) 50:311-313.
Koehler and Milstein, "Continuous cultures of fused cells secreting antibody of predefined speificity" Nature 256, 495-497 (Aug. 1975)
Leman ES et al., "Evaluation of Colon Cancer-Specific Antigen 2 as a Potential Serum Marker for Colorectal Cancer" Clinical Cancer Research 14(5):1349-1354 (2008).
Leman ES, et al., "Initial Analyses of Colon Cancer-Specific Antigen (CCSA)-3 and CCSA-4AS Colorectal Cancer-Associated Serum Markers", Cancer Res. 67 (12):5600-5605 (2007).
Sumedha, "Aptamers: An Emerging Class of Molecules that Rival Antibodies in Diagnostics" Clin. Chem. 45:9 (1999), 1628-1650.

* cited by examiner

| | | |
|---|---|---|
| M2-PK (+) Hb (+) | LEVEL 4 (RED) | 90% PROBABILITY FOR ADVANCED NEOPLASIA. COLONOSCOPY AS SOON AS POSSIBLE. 5 |
| M2PK (+) Hb (-) | LEVEL 3 (ORANGE) | MORE CLARIFICATION REQUIRED (E.G., COLONOSCOPY). |
| M2PK (-) Hb (+) | LEVEL 2 (YELLOW) | MORE CLARIFICATION REQUIRED (E.G., COLONOSCOPY). 10 |
| M2PK (-) Hb (-) | LEVEL 1 (GREEN) | COLON CANCER CAN BE EXCLUDED WITH 97 % SECURITY. 15 |

*FIG. 10*

SEQUENCE LISTING

```
<160> NUMBER OF SEQ ID NOS: 12

<210> SEQ ID NO 1
<211> LENGTH: 8
<212> TYPE: PRT
<213> ORGANISM: Homo sapiens

<400> SEQUENCE: 1

Leu Ala Pro Ile Thr Ser Asp Pro
1               5

<210> SEQ ID NO 2
<211> LENGTH: 8
<212> TYPE: PRT
<213> ORGANISM: Homo sapiens

<400> SEQUENCE: 2

Val Glu Ala Ser Phe Lys Cys Cys
1               5

<210> SEQ ID NO 3
<211> LENGTH: 9
<212> TYPE: PRT
<213> ORGANISM: Homo sapiens

<400> SEQUENCE: 3

Cys Ser Gly Ala Ile Ile Val Leu Thr
1               5

<210> SEQ ID NO 4
<211> LENGTH: 8
<212> TYPE: PRT
<213> ORGANISM: Homo sapiens

<400> SEQUENCE: 4

Thr Glu Ala Thr Ala Val Gly Ala
1               5

<210> SEQ ID NO 5
<211> LENGTH: 16
<212> TYPE: PRT
<213> ORGANISM: Homo sapiens

<400> SEQUENCE: 5

Leu Arg Arg Leu Ala Pro Ile Thr Ser Asp Pro Thr Glu Ala Thr Ala
1               5                   10                  15

<210> SEQ ID NO 6
<211> LENGTH: 9
<212> TYPE: PRT
<213> ORGANISM: Homo sapiens

<400> SEQUENCE: 6
```

```
Lys Cys Cys Ser Gly Ala Ile Ile Val
1               5

<210> SEQ ID NO 7
<211> LENGTH: 8
<212> TYPE: PRT
<213> ORGANISM: Homo sapiens

<400> SEQUENCE: 7

Glu Ala Glu Ala Ala Ile Tyr His
1               5

<210> SEQ ID NO 8
<211> LENGTH: 8
<212> TYPE: PRT
<213> ORGANISM: Homo sapiens

<400> SEQUENCE: 8

Ser Gly Ala Ile Ile Val Leu Thr
1               5

<210> SEQ ID NO 9
<211> LENGTH: 6
<212> TYPE: PRT
<213> ORGANISM: Homo sapiens

<400> SEQUENCE: 9

Leu Gln Leu Phe Glu Glu
1               5

<210> SEQ ID NO 10
<211> LENGTH: 8
<212> TYPE: PRT
<213> ORGANISM: Homo sapiens

<400> SEQUENCE: 10

Gln Leu Phe Glu Glu Leu Arg Arg
1               5

<210> SEQ ID NO 11
<211> LENGTH: 7
<212> TYPE: PRT
<213> ORGANISM: Homo sapiens

<400> SEQUENCE: 11

Val Glu Ala Ser Phe Lys Cys
1               5

<210> SEQ ID NO 12
<211> LENGTH: 8
<212> TYPE: PRT
<213> ORGANISM: Homo sapiens

<400> SEQUENCE: 12

Lys Ser Gly Arg Ser Ala His Gly
1               5
```

TEST KIT (COMBINED QUICK TEST) FOR THE SYNCHRONOUS PROOF OF BIOMARKERS IN FAECES FOR DETECTING OF PATHOLOGICAL CHANGES IN THE GASTROINTESTINAL TRACT, PARTICULARLY IN THE INTESTINE

FIELD OF THE INVENTION

The invention relates to a commercially applicable, cost-reducing, novel test kit (combined rapid test cassette), in vitro medical device, lateral flow cassette, point of care test, combined rapid test, bioassay, rapid lateral flow test strips, platform), for carrying out a method for detecting biomarkers in human and/or animal stool. The test kit is used for health analysis, early detection and "colon cancer prevention" by the detection of biomarkers that can provide an indication of pathological changes particularly of a malignant event in the gastrointestinal tract (esophagus, stomach, small bowel, biliary tract, pancreas, and colon), particularly tumors and tumor precursors (polyps, adenomas) of the bowel. The invention relates more particularly to a combined rapid test and a combined rapid test cassette and to the components thereof as well as to the necessary reagents for the synchronous execution of an immunochromatographic detection method. Synchronous in the linguistic meaning of "simultaneous", but synchronous also in the technical meaning of the common optimum coordination of active pairings (the chromatographic conditions, membranes, reagents, dispensing rate, etc., see descriptions) for detecting two biomarkers tumor M2-PK and hemoglobin in a combined rapid test cassette.

The invention further relates to a simpler method for evaluating the test and the presentation of the results ("risk impact scheme" using the colors of a traffic light).

The combined rapid test is used for "pre-filtering" probands in a colon cancer screening program. Since carrying out the non-invasive combined rapid test causes significantly less anxiety than performing an invasive colonoscopy in the proband, the test leads to an increased participation in colonoscopy.

BACKGROUND OF THE INVENTION

Cancer, particularly colon cancer is the most common cancer in Germany (65,000 new cases, 27,000 fatalities). In Europe, 200,000 people per year die of this treacherous disease. Due to the mode of origin of colon cancer, the consequences of colon cancer diseases can significantly be minimized by successful screening, i.e., the detection of precursors (polyps/adenomas) and their removal.

Every 20 minutes a person in Germany dies of colon cancer. Colon cancer almost always develops from initially benign growths of the intestinal lining (mucosa). The cancer grows slowly and for a long time without the affected person noticing it. Usually, symptoms only appear when the tumor is large or has already metastasized. If left untreated, colon cancer then often leads to death within 12 months.

Because of its mode of origin, the consequences of colon cancer can nearly completely be prevented by a successful screening of asymptomatic probands.

Precursors (polyps/adenomas) can be detected early by screening measures. Colonoscopy is considered the best method (gold standard) for the early detection of colon cancer. Colonoscopy is an invasive method to be performed by specially trained physicians only (e.g., gastroenterologists). This procedure is associated with risks (e.g. performation, risks by sedation). Preventive colonoscopy is covered by medical insurance for all people aged 55 and over. The participation rate is however only 2-3%, and in spite of considerable educational efforts and marketing campaigns, "glamour world actions", is today even declining! The reason for this resides, among other things, in the procedure of the examination which many people find unpleasant (psychological inhibition threshold).

OBJECT OF THE INVENTION

1. Reducing the psychological inhibition threshold.
2. Increasing the participation rate in screening colonoscopy.
3. Calibration (removal of quality differences).
4. Standardization.
5. Increasing the diagnostic accuracy.

Solution

Providing a simple, robust, inexpensive, routine-suitable lateral flow test, which is also suitable, by the synchronous detection of two specific biomarkers (M2-PK and hemoglobin), for detecting abnormal gastrointestinal diseases, especially colon cancer and its precursors. The combined rapid test that is simple and can easily be performed, is suitable to reduce the psychological inhibition threshold in view of the screening colonoscopy. The positive diagnosis of only one biomarker, M2-PK and/or hemoglobin, will already cause the physician to carry out a colonoscopy for further diagnosis. This will lead to a higher detection rate of colon cancer and its precursors by the colonoscopy, since with the previous combined rapid test a pre-selection of the probands is achieved. Since the combined rapid test synchronously determines two important biomarkers for colon cancer, this test serves as a dual filter before the colonoscopy.

Colon cancer with its precursors (polyp-cancer sequence) starts on the inside of the bowel (mucosa) and then expands into other areas of tissue (submucosa, muscularis, serosa). Tumor growth beyond the mucosal boundary is called a colon cancer in an early or advanced stage. Since the stool has direct contact with the mucosa of the bowel, biomarkers can earlier and more specifically analytically be detected as indicators of pathological changes in the gastrointestinal tract than in blood. For this reason, stool samples are preferred over blood samples. Only when the tumor has reached the submucosa, early biomarkers are detectable in the blood. When these markers are detectable in the blood, they are "late" forms of colon cancer and its precursors. Generally, the measurement of biomarkers in the stool is advantageous compared to the measurement of biomarkers in the blood. The sooner a cancer and its precursors are detected, the better is the prognosis. The initiated therapy (e.g. curative colonoscopy, "small visceral" surgery) leads to an almost 100% cure of early stage colon cancer.

The colonoscopy is considered the "gold standard" for examining a malignant, in particular tumoral process in the bowel.

Only specially qualified physicians are allowed to carry out the colonoscopy. Colonoscopy further has the disadvantage that it is not standardized. Further, the "wrong" probands are colonoscopied. During the bowel examination (colonoscopy), which is a key component of early detection, about 70% of the diagnoses are within normal limits. In only about a quarter of the cases, precursors are diagnosed, and in 1% of the cases, a carcinoma is diagnosed. The screening colonoscopy is therefore a very inefficient and furthermore expensive screening method, since too many healthy probands are colonoscopied (reduce healthcare costs!).

Therefore, it is desirable to perform before, the colonoscopy, a non-invasive, inexpensive and sensitive, reliable test that synchronously measures multiple biomarkers, in order to forward probands with a positive test result in a targeted manner to the colonoscopy (reduction in mortality). By means of the non-invasive combined rapid test according to the invention, the participation rate in a screening program for detecting colon cancer and its precursors can greatly be increased, and therefore a significant increase in the survival rate of patients (as opposed to probands!) having colon cancer or its precursors can be achieved. If colon cancer and its precursors are detected in time, this results in an almost 100% chance of recovery for the patient. Diagnosis: Increased M2-PK levels and/or hemoglobin levels lead, with the aid of anamnesis, etc., to the initiation of a "package" of measures and to further steps leading to the diagnosis of colon cancer. The diagnosis in turn leads to instructions for the physician, e.g. surgical therapeutic measures, and these in turn lead to the cure of colon cancer. E.g., a therapy by surgery may reduce the fatality rate.

In in vitro tests, too, same as in all diagnostic methods, the so-called sensitivity and the so-called specificity are the decisive quality features. Sensitivity is the probability to identify a diseased individual as such. This quality measure is very important in the medical field, since in an early detection measure, of course, as few sick people as possible should be overlooked. Specificity is the probability to identify a healthy person as such. This measure, too, is important for early detection, as it should be avoided that healthy people who are wrongly diagnosed as sick, receive an unnecessary treatment.

State of the Art

Guaiac Test (gFOBT) (Sample Material: Stool).

This chemical stool test is based on the guaiac resin. Through a chemical redox reaction, hidden (occult) blood amounts are detected in the stool samples of patients. As this chemical test is based on a redox potential, and this redox potential is disturbed by oxidizing agents and reducing agents, there will be disturbances of the test, and a low sensitivity and specificity will result. The oxidizing agents and reducing agents are contained in the food. Therefore, this test has a low sensitivity and specificity and is therefore considered outdated and obsolete. In addition, it is known that only heavily bleeding forms, not however weakly bleeding forms of colon cancer or its precursors can be detected. Furthermore, it is known that there exist bleeding, non-bleeding, and intermittently bleeding forms of cancer and its precursors. Depending on the time of sampling, therefore, colon cancer and its precursors may be overlooked.

Immunological Stool Test (iFOBT) (Sample Material: Stool).

Immunological in vitro tests also search for occult blood that finds its way into the stool by precursors (polyps) or early stages. Detection is achieved by using specific antibodies against hemoglobin or against the hemoglobin/haptoglobin complex. More than 10 manufacturers/distributors offer these iFOB tests. However, the tests offered in the market show extreme differences in quality (with respect to sensitivity and specificity), only specialists can recognize these differences, not however, as desired, the large number of general practitioners (users).

Furthermore, it should be mentioned that these so-called blood in stool tests only indirectly detect colon cancer and its precursors, as they are not specific for cancer and its precursors, but only for detecting blood (non-specific for colon cancer). These tests can only detect, same as the classic guaiac tests (gFOBT), bleeding forms of colon cancer or its precursors. Besides, it is known that there are bleeding, non-bleeding, and intermittently bleeding forms of colon cancer and its precursors. Depending on the time of measurement, thus, colon cancer and its precursors might be overlooked.

By using the gFOBT and the iFOBT tests, only bleeding tumors and their precursors can be detected.

Therefore, these tests may "detect" and "over-look" colon cancer and its precursors.

General:

Casually and pathophysiologically, therefore, occult blood in the stool is only indirectly related to colon cancer and its precursors!

Enzymatic Stool Test (M2-PK) (Sample Material: Stool).

This is a test that cannot detect occult blood in the stool, but an enzyme that is typical for cancer. This enzyme always occurs in larger quantities in malignantly modified tissue of various cancers—also including colon cancer or malignantly modified colon polyps. This test, which is also available on the market in the formats of the lateral flow test and ELISA, detects the biomarker tumor M2-PK. The tumor M2-PK is a special isoenzyme of the pyruvate kinase (PK). In normal tissue, the pyruvate kinase (M1-, M2-PK form) occurs as a tetrameric form (M2-PK tetrameric). In cancer and its precursors, the dimeric form of this PK (M2-PK dimeric =tumor M2-PK) is found more and more often. Against this particular tumor M2-PK molecule, two different monoclonal antibodies have been generated. These special antibodies specific for tumor M2-PK can be used in the tests available on the market (used in the ELISA and/or lateral flow formats).

General:

Casually and also pathophysiologically, the biomarker M2-PK is directly related to cancer and its precursors. The enzyme M2-PK (dimeric form of the isoenzyme M2-PK) is always detectable in all tumors examined up to now (e.g., 12 tumors of different tissues/organs), also in colon cancer and its precursors.

Clinical studies have shown that the tumor M2-PK tests on the market (in the lateral flow and/or ELISA formats) can detect both bleeding and non-bleeding colon cancer and its precursors.

These tests (test strips) may however also "over-look" colon cancer and its precursors. Therefore, it is a further object of the present invention to offer improved M2-PK tests (test strips).

Technical Solution:

A test kit according to the invention including a combined rapid test consisting of a plastic cassette as well as two novel test strips being improved over prior art for determining the M2-PK and the hemoglobin ("iFOBT", "immunological test", "occult blood test").

Blood Test (Sample Material: Blood).

Tumors release DNA (and/or methylated DNA) into the bloodstream. In this way, colon cancer leaves a typical signature—a biomarker. This biomarker is detectable with a blood test. For this purpose, the physician takes a blood sample from the proband and sends it to a specialized laboratory for a relatively complex, expensive measurement and evaluation by means of a PCR technology not being very robust for everyday use.

General:

Casually and also pathophysiologically, a DNA methylation pattern, a signature, a typical trace (biomarker SEPT9, septin-9 blood test) is only indirectly related to cancer and its precursors.

The M2-PK can only detect bleeding and non-bleeding tumors and its precursors. But the M2-PK tests, too, "overlook" colon cancer and its precursors. Therefore, it is an object of the present invention to achieve an improvement. This object is achieved by the claims and the technical description of the present invention.

A disadvantage of the previously known tumor M2-PK tests (in the lateral flow PCT/EP00/09303 and/or ELISA formats) as well as of the gFOBT and iFOBT is that none of the three tests, taken by itself, covers the entire diagnostically relevant period of time, in particular in relation to the patient.

From the WO 2007/071366 A1 (Roche Diagnostics GmbH) a method is known, in which both the tumor M2-PK and the hemoglobin in the stool are determined. The quantitative determination of both parameters is performed in two separate tests, the evaluation should be made through a mathematical algorithm. In the description of the above document, a number of possible methods are mentioned, which can be the basis for the development of such an algorithm (see page 7, line 12-page 9, line 21), without an evaluation algorithm actually being revealed. The technical teaching of the document therefore relates to a method for searching an evaluation algorithm only.

An approach for a complete diagnostic detection/finding of all phases of the polyp-cancer sequence is not described in the prior art.

It was the object, therefore, to develop a test for detecting colon cancer and its precursors, which makes it possible to reliably and completely detect, in a single test, all diagnostically detectable phases of the polyp-cancer sequence. The test should allow the synchronous determination of hemoglobin and tumor M2-PK.

This object is achieved by the method according to the invention for diagnosing/detecting pathological changes in the bowel by means of a test kit (combined rapid test) by the specific detection of hemoglobin and tumor M2-PK. With the aid of the method according to the invention, it is possible to safely and very early detect pathological changes already when any one of the above analytes (hemoglobin, tumor M2-PK) appears.

Surprisingly, it has been shown that by the use according to the invention of the combined rapid test and of two novel, improved test strips for determining M2-PK and hemoglobin, as well as the necessary reagents for synchronously carrying out the immunochromatographic detection method, the technical problem, the increase of the overall sensitivity compared to the use of two biomarkers on two separate cassettes or one cassette, can be solved.

Therefore, the invention relates more particularly to a combined rapid test and a combined rapid test cassette and components as well as the necessary reagents for synchronously carrying out an immunochromatographic detection method. Synchronously in the linguistic meaning of at the same time, but synchronously also in the technical meaning of the common, optimum coordination of active pairings, chromatographic conditions (especially for the two novel test strips) for detecting the two biomarkers M2-PK and hemoglobin in a combined rapid test cassette.

However, this was only possible by the optimization of the cassette and all components (selection of the membrane and specification (capillary flow rate, etc.)), the selection of the so-called backing, the selection of detergents and solubilizing agents, liquid spreading vs. protein spreading, specificity of the selected membrane (e.g. nitrocellulose vs. nylon), sample pads selection and specification, conjugate pads selection and specification, absorbent pad selection and specification, adhesive card selection and specification, housing (plastic cassette, dual cassette) selection and specification, manufacturing schemes.

In vitro diagnostic test strips based on the immunochromatographic principle have long been known in prior art. Considering an immunochromatographic test strip from the design stage through all product improvements to the final manufacturing process, then all the principles of biology, chemistry, physics, and engineering are employed.

The following patent numbers describe relevant technical teachings with respect thereto: e.g., U.S. Pat. Nos. 433,734, 4,376,110, 4,435,504, 4,703,017, 4,855,240, 4,954,452, 5,028,535, 5,075,078, 95/16207, 5,654,162, EP 0810436 A1.

Test cassettes with more than one test strip (combined test cassette) in one test cassette belong to prior art (drug detection by strip test). Further, these cassettes are known for determining the hemoglobin/haptoglobin complex and hemoglobin. Only single test cassettes are known up to now for the synchronous determination of M2-PK and hemoglobin. Both tests alone "overlook" many pathological changes. The reason for this is, among others, the "poorly" set cut-off of the test strip and the poorly selected chromatographic conditions of the test system. A challenge for the manufacturer of a test system is the optimum selection of the so-called "cut-off". In principle, this cut-off can be taken from the histogram of the measured values of the proband population. The technical problem is the distinction between "healthy" and "diseased" probands. This is technically solved by the test kit and by providing the two novel test strips with an improved cut-off and the chromatographic conditions. The significance of the cut-off is explained in a study by van Rossum, without a test kit being known that would disclose the measurement of hemoglobin and tumor M2-PK using an optimized cut-off.

It is an object of the present invention to improve the cut-off and the poorly selected chromatographic conditions. This is technically achieved, according to the invention, by providing a test kit, a combined rapid test cassette, which contains two novel test strips with "well" adjusted cut-off, as well as the well selected chromatographic conditions for carrying out the combined rapid test.

From the documents WO 01/21826 A2, WO 02/50546 A2, and WO 03/069343 A2, different methods for detecting tumor markers for tumors of the gastrointestinal tract are known, in which the stool of a proband is examined for tumor markers. These methods have proven successful in practice, but still exhibit a high number of false negative and/or false positive results. This is improvable.

On the other hand, various methods for detecting tumor markers for tumors are known, which are based on the detection of tumor markers in blood or serum (see, e.g., Anticancer Research 19:2785-2820 (1999); WO 03/065003 A2, Leman E S, et al., Cancer Res. 67 (12):5600-5605 (2007), and Leman E S et al., Clinical Cancer Research 14:1349-1354 (2008)). While, on the one hand, this would be advantageous to diagnose a tumor disease at all, the detection of a biomarker for various tumor diseases, on the other hand, does not permit reliable information about the nature and localization of the affected organ or tissue, since tumor markers are in the rarest of cases really tissue-specific, and thus in the case of a positive result of a blood analysis for the tumor marker, no reliable conclusion with regard to the affected tissue is possible. So there are additional costly and complicated diagnostic methods necessary to reliably determine the type of tumor being actually present. Markers in the blood, plasma, or serum are therefore mainly used for therapy and follow-up of tumors.

In addition, this detection method implies that tumor markers formed in the tumor find their way in sufficient amounts into the bloodstream or into the serum. In the early stage of the development of cancer, particularly colon cancer, sufficient amounts of these tumor markers do not yet find their way into the bloodstream, so that detection via blood or serum examinations is not possible.

Synchronous Detection of Biomarkers.

In addition, for synchronously, precisely detecting the biomarkers according to the invention (M2-PK and hemoglobin), the technical solution for the common coordination of the determination (of the reliable detection=no exceedance of the statistical confidence interval) of both biomarkers in a test cassette is required. That means the common chromatographic conditions. See FIG. 1 to FIG. 6.

This is achieved by selecting the common, optimum coordination of the chromatographic conditions for detecting the two biomarkers M2-PK and hemoglobin in a combined rapid test cassette in the sense of a parameter selection according to the invention.

In particular by the optimization of the cassette and the components thereof (selection of the membrane and specification (capillary flow rate, etc.)), the selection of the so-called backing process, the selection of detergents and solubilizing agents, liquid spreading vs. protein spreading, specificity of the selected membrane (e.g., nitrocellulose vs. nylon), sample pads selection and specification, conjugate pads selection and specification, absorbent pad selection and specification, adhesive card selection and specification, housing selection and specification, manufacturing schemes.

The production of this combined cassette according to the invention with two test fields (using nitrocellulose membranes) is carried out according to the in vitro diagnostic devices (IVD) Directive 98/79/EC, and in accordance with ISO 13485 and the quality management QM ISO 9001.

Technical Problem:

Poor clinical sensitivity and specificity by the applied screening methods (gFOBT, iFOBT, tumor M2-PK, screening colonoscopy).

OBJECT OF THE INVENTION

Improvement of the clinical sensitivity (positive predictive value) and specificity (negative predictive value), in particular of the sensitivity.

Technical Solution.

The use of the combined test cassette according to the invention, whereby significant advantages (higher overall sensitivity) over the use of two test cassettes (possibly of two different manufacturers) will be achieved. In the prior art, there exists a lateral flow test (ScheBo M2-PK Quick Test) for the target introduction of colonoscopy to asymptomatic probands.

Technical Problem:

Improvement of the sensitivity and specificity.

Technical Solution:

The use of the combined test cassette according to the invention, which enables the synchronous immunochemical determination of biomarkers occult blood and tumor M2-PK.

The combined test cassette according to the invention contains two lateral flow test strips. Both test strips do not correspond to prior art, but represent each a better lateral flow test method according to the invention. I.e., there is on the combined test cassette in the preferred embodiment of the invention an optimized tumor M2-PK test=M2-PK plus test and an improved iFOB test=iFOB plus test, compared to prior art.

The synchronous (in the technical meaning) detection of the biomarkers tumor M2-PK and hemoglobin with coordinated cut-offs in a combined cassette (a test kit with all necessary reagents and components for carrying out the test) has advantages over time-shifted processing (determination) of both biomarkers (tumor M2-PK and hemoglobin) by means of two lateral flow cassettes (two test kits having two different set-ups of reagents and components for carrying out the test), since the specific solid phase/liquid phase antibodies as well as all required reagents and components of the combined test kits are well coordinated. Example: if a user would buy the ScheBo lateral flow test for determining the tumor M2-PK and another lateral flow test from another manufacturer for determining the hemoglobin and process them in a time-shifted manner, he or she would achieve a worse clinical sensitivity and specificity by means of these different and non-coordinated tests.

Objects and technical solutions of the invention:
1. Reducing health care spending by targeted introduction to colonoscopy.
2. Providing a targeted, simple, manageable "entry diagnostics" for early detection of colon cancer.
3. Improving the prognosis of an individual colon cancer disease by early detection by means of providing the combined rapid test cassette according to the invention for the synchronous determination of tumor M2-PK and iFOB-determination for the optimized selection of such individuals (probands), which require a specific entry diagnosis by colonoscopy. The technical problem of the pre-selection for colonoscopy can be solved with a combined rapid test cassette according to the invention. Only such probands who were positively diagnosed in the measurement of the analytes (tumor M2-PK and/or iFOB test) are subjected to colonoscopy in a targeted manner. The combined rapid test cassette according to the invention technically acts as a dual "filter" in the selection process.
4. Providing a lateral flow dual test cassette according to the invention and all associated reagents, specific antibodies (anti-tumor M2-PK (special epitope), anti-hemoglobin (special epitope)) that have specific physicochemical properties, e.g., specific binding constant and specific kinetic characteristics. Further, the selected solid-phase and liquid-phase antibodies, which are directed against the two different analytes, have, e.g., in the lateral flow measuring method specific properties (e.g., compatibility with glass fiber, nitrocellulose membrane, good coupling properties to, e.g., gold colloid).

5. Using specific antibodies in the combined rapid test that are both specific in their binding property for tumor M2-PK or hemoglobin and can be used in immunochromatographic methods (e.g., are "membrane-suitable", "detergent-suitable").
6. Reducing the mortality from colon cancer by providing a combined rapid test according to the invention for the targeted introduction to the invasive method—colonoscopy—and thus to a targeted preparation (according to "diagnostic" measures—decision tree/decision matrix) for a therapeutic procedure (surgery, chemotherapy).
7. Optimizing cost/benefit of the screening measures with regard to the detection of colon cancer and its precursors.

From the document WO 01/21826, it is known that the tumor M2-PK can be detected on a test strip by means of a chromatographic process. Thus, for example, in this test, a test strip (nitrocellulose) can be used, on which the required antibodies are arranged either in a soluble form or in a fixed solid phase in various zones of the test strip. The sample (e.g. stool extract, a mixture of many substances, but also the analyte to be detected in detergent solution) or the liquid portion of the sample or an extract can migrate through the test strip and create a signal at the detection site, if, e.g., tumor M2-PK and/or hemoglobin is present in the sample. The use according to the invention of highly specific capture antibodies ensures the binding of the target proteins (e.g., tumor M2-PK) from the stool sample extract. By using gold colloids, on which a second highly specific antibody is present, an immune complex is formed in the presence of, e.g., tumor M2-PK. This analyte detection complex can be seen with the naked eye as a line on the test strip. The exact arrangement of the individual components on a test strip is dependent on the applied immunological methods and is known by the person skilled in the art. A particular challenge is the use of the optimum antibodies. In the combined rapid test according to the invention, special antibodies that specifically bind the tumor M2-PK were used.

The tumor M2-PK-specific antibody binds (also stereospecifically the dimeric form of the M2-PK) to one of the following epitopes or fragments thereof that have a length of at least four amino acids:

| | | | |
|---|---|---|---|
| LAPITSDP | (SeqID 01) | EAEAAIYH | (SeqID 07) |
| VEASFKCC | (SeqID 02) | SGAIIVLT | (SeqID 08) |
| CSGAIIVLT | (SeqID 03) | LQLFEE | (SeqID 09) |
| TEATAVGA | (SeqID 04) | QLFEELRR | (SeqID 10) |
| LRRLAPITSDPTEATA | (SeqID 05) | VEASFKC | (SeqID 11) |
| KCCSGAIIV | (SeqID 06) | KSGRSAHG | (SeqID 12) |

The occurrence of one of these epitopes or fragments thereof, which have a minimum length of four amino acids, or combinations thereof in a stool sample extract is an indication of pathological changes (colon cancer or its precursors) in the gastrointestinal tract.

The so-called blood in stool tests (gFOBT) exhibit an insufficient sensitivity of only 25% for detecting colon cancer. The tumor M2-PK test, in contrast, has a higher sensitivity of 80%. With the tumor M2-PK test, polyps greater than 1 cm can be detected with a sensitivity of 60% (FOBT: 20%), polyps smaller than 1 cm with a sensitivity of 20% (FOBT: 0%) (all values for a specificity of 95%).

Generally, immunochromatographic blood in stool tests show a higher sensitivity for colon cancer and its precursors than the gFOBTs normally used, therefore the gFOBTs are inferior to iFOBTs what concerns expressiveness.

The positive rates as well as the specificity and sensitivity are widely varying among these tests. The observed patterns suggest that the strongly different positive rates are based on different cut-off levels, different boundary areas, and limits of the tests of the various manufacturers from different countries. The production quality of the tests from different manufacturers varies, too.

Test kits from different manufacturers address different cut-offs (=tolerance limit, it denotes a tolerance value). The tolerance value specifies from when on a test result is considered positive or negative. The cut-off is to be distinguished from the concept of the limit of detection.

Lit: Inter-test agreement and quantitative cross-validation of immunochromatographic fecal occult blood tests, Hermann Brenner et al., Int. J. Cancer (2010).

As a consequence of this, a strong variation in the test characteristics of individual tests can be observed (technical problem). Hence, in the scientific literature, it is requested to make better test kits available and find and use optimized cut-offs offs (H. Brenner, S. Tao, European Journal of Cancer (2013)).

Further studies substantiate the high variance of test kits that are available on the market (Brenner et al., Int. J. Cancer, 2010). This results in a high need in the art for a test kit that is capable of indicating tumor M2-PK and hemoglobin in stool samples, using a cut-off, which guarantees the highest possible diagnostic efficiency.

This technical problem is solved by providing the test kit comprising the combined cassette containing two test strips being improved over prior art.

Cut-off levels, boundary areas and limits for both biomarkers have been found and determined by comprehensive in-house measurements. The determination was performed by descriptive statistical analysis and interpretation of the biomarker level histograms (box plot analyses and Kruskal-Wallis calculations). The production of both test strips and the adjustment of the chromatographic conditions for the synchronous determination of both biomarkers for achieving better clinical sensitivities and specificities, represents a major challenge. This was technically solved by adjusting all chemical and physical conditions (see claims and examples). Thus, all conditions were chosen for determining the two biomarkers such that as few as possible "false positive" and "false negative" results are obtained when carrying out the combined test, in order that in this way the diagnostic efficiency, which indicates the ratio of all true positive and true negative test results relative to the total of all results, is significantly increased.

To achieve this goal, a technical solution was sought and found. For the technical solution, the synchronous detection, in the technical meaning, of the biomarkers under coordinated chromatographic and coordinated material conditions was found, i.e., the proper choice of the membrane, running conditions, etc. (see examples and claims).

Tumor markers are genetic products that are differentially expressed in tumor tissue, with respect to normal comparison tissue, i.e., a tumor marker is either over or underexpressed in tumor tissue, compared to normal tissue. For the practice, those tumor markers are more important, which are overexpressed, since then a positive analytical result (presence of the biomarker) of a sample is indicative of the presence of the biomarker-specific tumor. Tumor markers are present in the cytoplasm of the tissue cells, but may also exist in body fluids, such as blood, urine, sweat, semen, saliva, etc., but also in the stool.

A tumor marker should have the following properties: i) high specificity, i.e., not detectable for benign diseases and healthy persons, ii) high sensitivity, i.e., it can be detected in a high percentage of the tumor patients, iii) organ specificity, iv) good correlation with the tumor stages or the tumor mass, v) relationship to the prognosis, and vi) reliable prediction levels. The criteria of 100% specificity and 100% sensitivity and the other listed criteria are not met until now by any one the known tumor markers.

Inter alia, tumor markers specific for tumors of the gastrointestinal tract include CCSA-2, CCSA-3, CCSA-4, CC2, CC3, CC4, CC5, CC6a, CC6b, L1, L2, N1, N2, N3, N4, N5, and N6 (see, e.g., WO 03/065003 A2; Leman E S, et al., Cancer Res. 67 (12):5600-5605 (2007), and Leman E S, et al., Clinical Cancer Research 14:1349-1354 (2008)). These tumor markers are, however, used in prior art in the context of blood plasma tests only, leading to the disadvantages mentioned above.

It is desirable to be able to detect as soon as possible a tumoral event in the gastrointestinal tract, especially in a growth phase, in which the tumor has not yet accomplished contact with the vascular system of the body (for example, already in the "polyp-cancer sequence", i.e., at a time before the infiltration of the submucosa). In case of a suspected neoplastic event in the gastrointestinal tract, particularly with regard to the so-called adenoma-carcinoma sequence in polyps, it is attempted, in prior art, to detect occult blood in the stool by means of various methods of determination. For this purpose, non-immunological tests (e.g., pseudoperoxidase activity, porphyrin detection) and immunological tests are employed (Favenne L. et al., (1992) Ann. Biol. Clin. 50:311-313).

However, both test principles are not very specific. In addition, the non-immunological test based on a redox reaction (test principle) can be disturbed by a variety of factors (false positive/false negative, e.g., by non-compliance with absolutely needed dietary requirements on the part of the patient and of a number of drugs and by excessive vitamin C administration (e.g., in vegetables, fruit juices, etc.), Thomas L., Labor and Diagnose, 5th edition, 1998.

A positive test for occult blood in the stool must be clarified for such a time until the bleeding source was located or the cause of the bleeding was found. The clinical diagnosis justifies in any case rapidly performed further diagnostics ("diagnosis by exclusion"), e.g., by endoscopy, ultrasound, X-ray.

TECHNICAL PROBLEM OF INVENTION

The existing prior art M2-PK lateral flow test (test strip) overlooks pathological changes.

The M2-PK plus test strip according to the invention also overlooks pathological changes.

The existing prior art iFOBT overlooks pathological changes.

The iFOBT plus test strip according to the invention overlooks pathological changes. If both improved tests M2-PK plus and iFOBT plus are brought together, according to the invention, as test strips in a combined cassette, a higher recognition rate for pathological changes in the bowel are obtained according to the invention. Technical solutions of the problem, in particular the selection of active pairings (see examples and list the components and active ingredients according to the invention, the right choice of the antibodies and the right choice of the cut-offs for both parameters, the analytical sensitivity, capillary flow rates, etc.) for the synchronous detection of the two biomarkers are the subject matter of the parameter selection according to the invention.

It is therefore the technical object of the invention to specify a test kit of simple construction (combined rapid test), which serves as a method for detecting markers, biomarkers, particularly enzyme biomarkers in human or animal stool, the method being suitable for detecting a malignant event in the gastrointestinal tract and the abdominal cavity (esophagus, stomach, small bowel, biliary tract, pancreas, and colon), in particular of tumors and tumor precursors of the bowel (polyps, adenomas).

The combined test kit (combined rapid test) according to the invention is intended for allowing, in a simple manner, the detection of pathological changes, so that the test can be carried out by technical personnel.

In particular, it is the technical object of the invention to meet the continuously increasing demand for specific, easily carried-out methods, so that a pathological event, especially a neoplastic event can be detected particularly early and doubtlessly, particularly with regard to the problem of the so-called adenoma-carcinoma sequence with polyps.

PRINCIPLES OF THE INVENTION AND PREFERRED EMBODIMENTS

For solving this technical problem, the invention teaches a test kit (combined rapid test) for detecting a pathological event in the gastrointestinal tract, in which a sample of human or animal stool, dissolved in a special extraction buffer, is applied on a carrier, and both tumor M2-PK and hemoglobin are detected on a support. Here, reading takes place in a simple manner visually with the naked eye (without the use of a device).

In a preferred embodiment of the invention, hemoglobin is determined in the form of the hemoglobin/haptoglobin complex (Hb/Hp). It has been found that the measurement of the above mentioned biomarkers is particularly suitable for detecting early malignant changes, especially neoplasms. By measuring this biomarker combination tumor M2-PK plus hemoglobin; tumor M2-PK plus hemoglobin/haptoglobin complex (Hb/Hp), a marked improvement in preciseness of statements (reporting) is achieved, in particular a significant decrease of the false negative, but also of the false positive diagnoses.

This is particularly surprising, since extensive studies with respect to other specific analytes (proteins) in the stool did not allow any evidence of their application as biomarkers, especially as tumor markers. Both the structure and the physico-chemical properties of the mentioned tumor markers obviously are not affected as a result of the significant proteolytic activity and the extreme physiological conditions (e.g., pH, acid in the stomach, alkaline in the bowel) of the gastrointestinal tract. This also applies to the detection of the biomarkers by means of immunological methods. It was therefore found and shown that despite the above-mentioned protein denaturation and protein digestion in the gastrointestinal tract, a specific detection of several enzyme biomarkers in the stool of tumor patients can be carried out.

The systems necessary for determining the enzyme biomarkers are commercially not readily available. For developing the combined rapid test according to the invention, both the detection limits as well as the composition of the reagents (according to the invention: specific antibodies for the liquid and for the solid phase for both analytes, optimized for the synchronous measurement of the analytes), and suffer solutions, detergents, etc., had to be adjusted in an extremely costly manner.

In an M2-PK and/or hemoglobin-positive stool sample, thus, an indication of a pathological, potentially neoplastic, particularly malignant event in the gastrointestinal tract is immediately obtained, i.e., in particular in the bowel, esophagus, stomach, biliary tracts, pancreas, or/and colon, and thus a localization of the event in the gastrointestinal tract is enabled.

It should be noted that a stool sample cannot be considered as a "body liquid" sample, as the entire gastrointestinal tract is, biologically, located outside the body.

With the method according to the invention it is now possible to detect in a non-invasive method in a simple manner a malignant tumor event in the stool by determining a plurality of said tumor marker proteins, and at the same time to be able to clearly define, with a positive test procedure, that a tumor is present in the gastrointestinal tract and not elsewhere in the body.

By this method, it is not only possible to generate an "initial suspicion", a "primary diagnosis", a diagnosis, but also follow-up is possible. Because of the individual protein distribution, an individual diagnosis is possible.

Surprisingly, it is possible, with the combined rapid test according to the invention, to detect the said enzyme biomarkers as free proteins in the stool. This is further advantageous, since the test can be carried out by assistants, for example, by a medical-technical assistant (MTA). Due to the fact that the two analytes (tumor M2-PK and hemoglobin) are synchronously determined, in particular reading errors (for example, by the MTA) are avoided, since for carrying out the test, the two sample drops of a patient are successively applied (naturally, with a few seconds delay), and after a certain period of a few minutes, both results are read. By this procedure, not only a higher convenience of the test procedure, but also a reduction of sources of error (in comparison with conventional tests) is achieved.

For the test according to the invention, an isolation of cells from the stool and an analysis of the proteins contained in the cells is not required. For it was found out that solid tumors release the mentioned enzyme biomarkers as soluble proteins into the lumen of the gastrointestinal tract, and these biomarkers are not present in flaked-off gastrointestinal epithelial cells. Said enzyme biomarkers are released from tumor cells, pass through the gastrointestinal tract as a protein, and can finally be detected as a protein in the stool. This possibility, namely that these proteins remain detectable in the stool after, e.g., passing the stomach and the bowel, could not be expected, since normally a high degree of decomposition of the respective proteins in the course of the normal digestive process would be expected.

In the context of the present invention, it was found out that said enzyme biomarkers remain quantitatively detectable even in highly homogenized stool samples having been stored for longer periods of time (for example, when samples are shipped). Even with strong dilution of the stool, a strong reaction is obtained. In addition, the detection can take place selectively in the stool sample, even without prior extraction. Preferably, however, an extraction method, for example, using a special detergent (e.g., CHAPS) is used (the extraction process is described in more detail in Example 2).

In the method according to the invention, preferably the malignant events in the gastrointestinal tract of a human or an animal are determined. Furthermore, it is preferred to immunochemically detect the tumor marker, in particular by means of anti-tumor marker antibodies. Monoclonal or polyclonal antibodies, preferably monoclonal antibodies, can be used. Advantageously, antibodies are used which do not cross-react with other components of the stool, in particular not with other stool proteins.

Fragments in the meaning of the invention are proteins or polypeptides having an amino acid sequence which is identical to a partial sequence of one of said tumor markers. The length of the fragment may be from 5 aa (aa =amino acids) up to n-1 aa (n =length of the tumor marker from which the fragment originates). Typically, the length is longer than 10 aa.

Antibodies to be used according to the invention can be produced in accordance with the prior art method. The person skilled in the art is well familiar with methods for producing specific monoclonal antibodies. For example, for this purpose, the antigen, i.e. in the present case an enzyme biomarker, is used for generating antibodies. In principle, this method, which was first described by Koehler and Milstein, can be used, however, modifications and further developments of these methods are also known by the person skilled in the art. By this type of production, specific antibodies can be obtained, wherein the specificity can be determined by selection. The selection is performed for specific antibodies, which bind to an enzyme biomarker, but not to other stool proteins.

In a particularly preferred embodiment, detection is made by using the principle of the immunoassay. An immunoassay preferred according to the invention is carried out in such a way that a) the sample is brought in contact with at least two different receptors, of which the first receptor R1 is present in a solid phase and is capable of binding to the tumor marker, and the second receptor R2 is present in the liquid phase and is also capable of binding to the same enzyme biomarker, wherein the receptor R2 carries a label or mediates the binding to a detectable molecule, b) the solid phase is separated from the liquid phase, and c) the label or the detectable molecule in one of the phases, preferably in the solid phase is determined and accordingly the amount of enzyme biomarkers present in the sample is quantified by using an antibody as at least one of receptors R1 or R2, said antibody being capable of specifically binding to the tumor M2-PK, and in particular to no other stool protein.

In a particularly preferred embodiment, an antibody against tumor M2-PK is used as a receptor R1 and also as a receptor R2. Tumor M2-PK is understood, according to the invention, as the dimeric form of this enzyme biomarker, which differs from the tetrameric form.

The determination of the hemoglobin takes place according to the test principle described above for tumor M2-PK.

In addition to carrying out the method according to the invention in the form of an immunoassay and in particular of an ELISA, other detection technologies can also be used, such as the crystal oscillator technology, micro-scale technology, lateral flow technology, candelabra technology, TRACE technology, or electrochemiluminescence technology, but also the agglutination with micro- or nanoparticles (measured by nephelometry) and multiplex technologies in the liquid or solid phase or array technologies, such as using protein chips. These technologies are familiar to the person skilled in the art and therefore need not be described in detail here.

Preferably, the lateral flow technology is used. Therefore, the subject matter of the present invention is a combined rapid test for the detection and/or suspected diagnosis of a malignant tumor event in the gastrointestinal tract in humans or animals, which is provided in particular for carrying out the method described above, by determining an enzyme biomarker combination, the combined rapid test synchronously determining tumor M2-PK and hemoglobin or hemoglobin/haptoglobin.

Preferably, the combined rapid test contains an antibody for tumor M2-PK that does not cross-react with any other stool protein, and an antibody that specifically detects hemoglobin/haptoglobin and does not cross-react with any other stool protein. If applicable, the test kit may optionally contain other reagents necessary for carrying out an immunoassay or for carrying out the respectively provided test procedure. Preferably, the kit contains an antibody being bound to a solid phase and being specific for at least one of said enzyme biomarkers.

Another subject matter of the invention are antibodies, in particular monoclonal antibodies, which specifically bind one of said enzyme biomarkers and preferably do not cross-react with any other stool protein. The antibodies can, for example, be produced by the method of Koehler and Milstein (Nature 256, 495-497 (1995)).

Furthermore, the present invention relates to aptamers or spiegelmers and to their use in place of the antibodies described above (all other antibody-related statements apply in an analogous manner), which specifically bind to one of said enzyme biomarkers and optionally do not cross-react with any other stool protein. Aptamers are oligonucleotide sequences, which have specific binding properties. Such aptamers can, for example, be produced or identified according to the methods described in U.S. Pat. No. 5,270,163 or in Sumedha, Clin. Chem. 45 (1999), 1628-1650. Spiegelmers are aptamers, which are formed from L-oligonucleotides.

The evaluation of the tests according to the invention is carried out by using the automatic classification, cluster analysis, pattern recognition. In particular, methods of the "maximum likelihood method" or the cluster membership via probability distributions are applied.

For the laboratory personnel and the attending physician, the result is preferably presented in the form a multi-colored illustration (risk impact scheme), decision matrix, and other algorithms for decision-making.

For example, the measured parameters (hemoglobin and M2-PK) can be assigned to as follows:

|  | M2-PK | Hb | Meaning |
| --- | --- | --- | --- |
| Level 1 (green) | − | − | Colon cancer can be excluded with 97% security |
| Level 2 (yellow) | − | + | More clarification required (e.g., colonoscopy) |
| Level 3 (orange) | + | − | More clarification required (e.g., colonoscopy) |
| Level 4 (red) | + | + | 90% probability for advanced neoplasia |

In any case, a kit according to the invention contains a sampling device for stool. For this purpose, all conventional devices can be used, for example, the devices described in DE 102 05 709 A1.

A particular challenge for achieving the optimum operating principle was the selection of the optimum active pairings. These active pairings are listed in the following examples, lists, and patent claims, and in particular in FIGS. 1-6.

For example, FIGS. 2, 3, 4 and 6 show different functions. A particular challenge for this invention was to select, under the numerous different functions (possibilities of combination), the optimum active pairings for achieving the optimum operating principle (selection of parameters).

In a particular embodiment of the invention, the evaluation is carried out automatically. For example, the test kit according to the invention can be photographed, and the test result can be assigned by an evaluation program to the appropriate level of risk. The present invention therefore also includes such devices for taking a photograph of the test kits and evaluation programs for the representation of the test results, preferably in the form of a multicolored display (risk impact scheme). An example of the assignment is shown in FIG. 10.

EXAMPLES

The invention is further explained by the following examples.

Example 1

Test Kit

The test kit based on an immunoassay consists of two sampling and preparation devices and a test cassette.

Both sampling devices contain a rod that is capable of receiving the required amount of stool (4-30 mg, preferably 25 mg). The sampling devices further include one tube each for receiving samples, which are filled with buffer solution.

The aqueous buffer solution for the tumor M2-PK test has the following components:

Buffer 1=10-70 mM phosphate buffer (pH 6.7 to 7.6) or buffer 2=10-70 mM HEPES buffer (pH 7.6 to 8.2) or buffer 3=10-70 mM triethanolamine (pH 7.3 to 7.7), preferred mixtures thereof volume 1:1:1 each.

Detergent 1=CHAPS (3-[(3-cholamidopropyl)dimethylammonio]-1-propane sulfonate, 10 mM-50 mM (Sigma), detergent 2=sodium dodecyl sulfate (SDS) 0.01%-0.1%), for example from Biochrom, detergent 3=lauryldimethylamine oxide (10 mM-50 mM), for example from Biochrom, or mixtures thereof.

The aqueous buffer solution for the hemoglobin test contains the following components:

Buffer 1=10-70 mM phosphate buffer (pH 6.7 to 7.6) or buffer 2=10-70 mM HEPES buffer (pH 7.6 to 8.2) or buffer 3=10-70 mM triethanolamine (pH 7.3 to 7.7), or mixtures thereof.

ANTIBODIES USED

The four antibodies required for the measurement (one each in the "liquid phase" and one antibody in the "solid phase") being antibodies capable of specific binding may be polyclonal antibodies, preferable however monoclonal.

The polyclonal and monoclonal antibodies are obtainable according to prior art by the classic methods of immunizing animals with the respective antigen or, preferably, by using the hybridoma method of Koehler and Mielstein.

Polyclonal and monoclonal antibodies that bind the human pyruvate kinase and also the isoenzymes of the pyruvate kinase, belong to prior art. Preferred are polyclonal antibodies and monoclonal antibodies that bind the dimeric form, i.e. the tumor form of the pyruvate kinase.

The quaternary structure of a protein relates to the spatial arrangement of the subunits of the protein.

"Normal M2-PK" has a tetrameric structure (quaternary form). The M2-PK of healthy persons is different from the "tumor M2-PK". "Tumor M2-PK" has a dimeric structure.

Polyclonal antibodies and monoclonal antibodies against these special forms (tumor M2-PK dimeric or M2-PK tetrameric) are obtainable by conventional immunization methods, as well as by the hybridoma method (Kohler-Mielstein technology).

Thus, the tumor form of M2-PK can be cleaned and used as an antigen. Another option is to buy genetically expressed M2-PK also in the tumor form and to use it for immunization. Another way is to synthesize specific fragments, i.e., amino acid sequences and to use them for the immunization.

TUMOR M2-PK ANTIBODIES

Preferred for spraying onto the nitrocellulose membrane is a monoclonal mouse antibody (clone PAT4M3AT, IgG1). This clone has been generated by hybridization of myeloma cells with B lymphocytes of the mouse. Recombinant human tumor M2-PK from E. coli with amino acids 1-531 was used as the immunogen. The antibody is available, amongst others, from the company ProSpec (East Brunswick, USA). Optionally, a monoclonal mouse antibody (clone AT1 E3, IgG1) can be used. Recombinant human tumor M2-PK was used as the immunogen. The antibody is available, amongst others, from the company Novus Biologicals (Littleton, USA). Particularly preferred for the coupling to the gold is a monoclonal mouse antibody (clone 1 E3, IgG1). Recombinant human tumor M2-PK with the amino acid seq 47-574 was used as the immunogen. The antibody is available, amongst others, from the company Novus Biologicals (USA). Optionally, a polyclonal antibody generated in sheep (Ig fraction) from the company Randox (United Kingdom) can be used. Recombinant human tumor M2-PK from E. coli served as the immunogen.

HEMOGLOBIN ANTIBODIES

Preferred for spraying onto the nitrocellulose membrane is a monoclonal mouse antibody (clone M1202100, IgG1). The antibody was produced by immunizing with human hemoglobin. The antibody is available, among others, from the company Thermo Scientific (Rockford, USA). Alternatively, a monoclonal antibody against human hemoglobin can be used. This antibody from the clone 7202 SPR-5 has an affinity constant of $1 \times 10^{-10}$ l/mol and an isoelectric point of 5.8. It can be obtained from the company Medix (Finland). For the hemoglobin antibody coupled to gold, the monoclonal mouse antibody (clone HB11-2312) was used. Purified human hemoglobin was used as the immunogen. The antibody can be obtained from the company Thermo Scientific (Rockford, USA).

One of the most important conditions for the selection of the antibody is that it does not cross-react with other components of the stool, especially not with other pyruvate kinase isoenzymes (e.g. M1-PK, M2-PK (tetrameric form) L-PK, R-PK).

The above hemoglobin antibodies are particularly suitable for binding to a membrane (solid phase), in a preferred form nitrocellulose. The antibodies mentioned above do not cross-react with hemoglobin from swine, horse, sheep, and cattle. The above hemoglobin antibodies are preferably suitable for binding to latex or nanoparticles—preferably gold colloids—(liquid phase). They do not cross-react with hemoglobin from sheep, horse, cattle, or swine. The antibodies bind hemoglobin A0 and A1 equally well, A2 partially with a lower binding constant, and AS partially with a very poor binding constant. Solid phase antibodies are preferably mixed 1:1 w/w. Liquid phase antibodies are preferably mixed 1:1 w/w.

Detergent 1 (CHAPS (3-[(3-cholamidopropyl)dimethylammonio]-1-propanesulfonate, 10 mM (Sigma)), detergent 2=sodium dodecyl sulfate (SDS) 0.01%-0.1%), e.g., from, detergent 3=lauryldimethylamine oxide (10 mM-50 mM), e.g., from Biochrom, or mixtures thereof.

The sampling device for carrying out the hemoglobin test contains one of the buffers described above (1.5-2.5 ml). The person being tested moves the dosing tip into the stool and transfers the stool sample into the empty tube filled with the corresponding buffer.

The sampling device for the tumor M2-PK test that the physician hands over to the person to be tested does not include any buffer. The patient moves the dosing tip into the stool and transfers the stool sample into the empty tube.

The test kit according to the invention further includes a test cassette, in which the two immunoassays being improved over prior art are carried out by lateral flow technology. For this purpose, the test cassette contains two preferably circular recesses for the application of the stool samples and two preferably elongate recesses for reading the test results.

The test cassette contains in its interior nitrocellulose with a preferred capillary flow rate of 135 sec/4 cm as the stationary phase.

During the investigations for the development of the test kit according to the invention, it has been found out that nitrocellulose has a strong influence on the spread of the results. This spread is particularly large in freshly prepared nitrocellulose, but becomes smaller after three to six months storage (maturation). The nitrocellulose used in the present invention has been stored for three to six months before being subjected to further testing. The use of such "matured" nitrocellulose enables a significant reduction in the spread of the results. In particular, it could be achieved that significantly lower variations occur between different batches of the produced test kits than for "fresh" nitrocellulose.

The antibodies are coupled to colloids, preferably gold colloids or latex colloids, preferably gold colloids with 20 nanometers in diameter.

The stationary phase=nitrocellulose (preferably with a capillary flow rate of 90 sec/4 cm) contains hemoglobin antibody 1, hemoglobin antibody 2, preferably in a mixing ratio as specified above.

The stationary phase =nitrocellulose (preferably with a capillary flow rate of 135 sec/4 cm) further includes tumor M2-PK antibody (from clone P1F3), tumor M2-PK antibody (from clone P5A1), preferably a mixture of antibodies of clones P1F3 and P5A1 in the following mixing ratio volume 1:3.5 w/w.

Antibodies from clone P1F3 and clone P5A1 are particularly useful as capture antibodies (stationary phase) for binding to a membrane, preferably nitrocellulose. Tumor M2-PK antibodies from clone P1A6 are preferred for binding to gold colloids or latex colloids, preferably gold colloids with 80 nanometers in diameter.

Devices and protocols for the test kit production, especially for the production of the two test strips:
Sealing device—film sealing device (company Kopp), packaging systems company Reichenbach.
Sealing temperature 60°, Type MSC 440 watts. Biodot device.
2. Biodot device.
Cutter of the company Zeta Corporation, www.zetacorporation.com, device type GC1800-081101.

Device is CE marked.
Protocol for laminating and cutting the nitrocellulose membrane number of laminated M2-PK cards.
Device setting and operation laminator Matrix 2210 of the company Kinematic.
Protocol for laminating and cutting the nitrocellulose membrane devices setting, operation laminator Matrix 2210.
Implementation device settings and operation.
Device settings and operation cutter GSI-800 of the company Zeta Corporation.
Production of cassettes and installing the ScheBo M2-PK Quick Kits.
Production of test cassettes.
Storage of partially finished products in refrigerators.
Quality control.
The temperature and humidity of the premises, where the production is made, is recorded.
Air conditioner FUJITSU DG Inverts for air conditioning and keeping the humidity and temperature constant. Compliance with the air temperature and humidity is of particular importance for the quality assurance of the test membranes.
Selecting the operating mode/setting the thermostat 1, setting the fan speed.
Critical success factors for the optimum coordination of the two test strips in the combined cassette are in particular:
  a) Heidelberger curves for Hb determination,
  b) Heidelberger curves for M2-PK determination.
Surprisingly, it has been found that when 6.7% ox gall (natural wetting agent, cleaned, from the company Schmincke, Part No. 50031, Schmincke, Erkrath, Germany) is admixed as a final concentration to the extraction buffer for M2-PK, particularly good reproducible immunochromatographic results are obtained.
Surprisingly, it has been found that when 2.8% ox gall is admixed as a final concentration to the extraction buffer for hemoglobin, particularly good reproducible immunochromatographic results are obtained.
Technical Synchronous Determination of the Two Analytes in the Combined Cassette.

For optimization of the "time shift" of the chromatography start time, the user starts the chromatography by dripping M2-PK stool sample extract into the left sample window of the cassette (then sets the timer to 5 minutes). Dripping of the Hb stool sample extract occurs after 1 minute after dripping the M2-PK stool extract into the right sample window of the cassette. I.e. the two chromatographies are started at shifted times. The result of the two tests is, however, read after expiration of the 5-minute stop time.

Chromatography, particularly immunochromatographic test methods depend—as the name implies—substantially on the time as well as the binding affinities (the binding of the antibodies to the antigens in the liquid and solid phase, as well as the various kinetics within the nitrocellulose membrane), i.e. they are subjected to various kinetics.

Test results, which are read later, are invalid! (All this is explained in the description of the combined test). The formation of the pink-red test line in the test region of the nitrocellulose test strip of the test membrane is biophysically the result of a complex agglutination reaction (various kinetics and affinities play a special role here, see also the Heidelberger curve to be described in more detail above).
Parallel, i.e. synchronous, in the technical meaning, processing or determining of the analytes according to the invention.
  1. Start of the "chromatography" M2-PK followed by a second start of the chromatography Hb.

The synchronous determination, in the technical meaning, is a challenge, since the immunochromato-graphic determinations are very complex.

Many parameters are of particular importance for achieving the multiple objects according to the invention:
  (All objects have been achieved at the ScheBo Biotech AG).

These objects have been achieved, according to the invention, by, e.g., the identification of specific/essential active pairings:
  1. Binding constant/affinity of the individual antibodies to the respective substances (proteins), the analytes according to the invention.

Another critical factor is also the composition of the "dried" gold and the "release" of the gold from the PAD release, i.e. the resolution of the dried gold particles (in a glass-fiber matrix/dried sugar matrix) by the dropwise addition of the extraction buffer, which contains the corresponding analyte (stool sample extract).

Preparation of the test kit according to the invention containing a dual cassette for immunochromatographic determination of two analytes.

In order to accomplish this, we first tested the immunochromatographic determination of the two analytes in a so-called dipstick format. This dipstick format is much less complicated, since it does not contain the conjugate release PAD.

The following tasks and challenges had to be solved according to the invention:
Nearly none of the technical solutions according to the invention were "obvious".
General Remarks:
For the preparation of the test strips, it is of particular importance to keep the humidity between 40 and 60% at 18° C. to 25° C.
By series of tests performed in the R&D department at the ScheBo-Biotech AG, an optimum humidity of 35% at 20° C. was determined in an inventive manner.
Tasks/Challenges:
  1a. Slowly flowing liquid in the membrane or even stop/interruption of the chromatographic liquid flow.
  1b. The sample in the liquid stops in the middle (in the flow direction of the membrane) of the membrane strip.
  Is the selected membrane too slow in flow speed for the application?
  Was the membrane turning hydrophobic?
  Has the correct wick been used?
  The nitrocellulose membrane contains "surfactants" and "wetting reagents".
  The test membrane has a high "background staining" (this background staining was solved by non-obvious solutions according to the invention).
  It is necessary to clarify whether specific blocking reagents are to be used.
  Set the release of gold onto the nitrocellulose membrane in an optimum and complete manner (solved by non-obvious solution according to the invention).
  The liquid front is not straight-lined (solved by non-obvious solution according to the invention).
  The test line is too thick or "fuzzy", "blurred" (solved by non-obvious solution according to the invention).
  A much too weak signal at the test line is reproducibly observed/found (solved by non-obvious solution according to the invention).
  The test line shows false positive/false negative results (solved by non-obvious solution according to the invention).

The test kit according to the invention contains metal colloids, preferably gold colloid. Specific embodiments are, e.g., latex particles, and also nanoparticles. Latex particles may be stained and also provided with fluorescent dyes and have different sizes (i.e. size in the micrometer range but also in the nanometer range).

Magnetic particles (initiate quantification using special reading devices (readers)) are also possible.

The major technical challenges were specifically related to quality assurance. Creation of good-manufacturing protocols (solved by non-obvious solution according to the invention).

Object/task: achieving an optimum, small inter- and inter-assay variance. Particularly important: very good lot-to-lot variance (i.e., a smallest possible lot-to-lot variance).

This small lot-to-lot variance is to be ensured in the context of quality assurance in the production process according to the invention (solved by non-obvious solutions according to the invention).

Production of a large number, more than 100,000 test kits with the same lot number, the same date of expiry (solved by non-obvious solutions according to the invention).

Challenge: ensuring extremely good quality—benefit for the customer (solved by non-obvious solutions according to the invention).

AGGLUTINATION—DEFINITION

In the medical field, agglutination designates the adhesion or clumping of cell pathogens, etc.

Agglutination reactions are used in laboratory diagnostics to make quantitative statements. The agglutination is measured by nephelometric determination methods.

The red test line is formed in a complicated kinetics by an agglutination reaction. In the three-dimensional structure of the nitrocellulose of the test strip, there occurs an agglutination. This "agglutination" is visible to the naked eye as a pink line.

This pink-red line is the result of a substance detection by an antigen/antibody reaction. This antigen/antibody reaction is subjected to a variety of effects. One of these effects is the so-called hook effect (also referred to as high dose hook effect), which takes place in falsely low determinations of analytes that occur in very high concentrations of sample solutions (i.e., high concentrations of the analyte in the particular case may feign false negative measurement signals).

Once the analyte concentration is too high, the antibody binding sites may be occupied by the analyte and the additional analyte molecules are no longer identified in the binding curve. There will be falsely low readings.

A technical object was to avoid the hook effect.

By parallel measurements of various dilutions of a sample, the presence of a high-dose effect can be noticed, and the measurement can be corrected accordingly (the object of the technical problem has been solved by non-obvious solutions according to the invention).

The test kit according to the invention described in the claims has, in contrast to the embodiments of prior art, no high dose hook effect. This could be shown in a convincing manner by tests with samples having tumor M2-PK concentrations exceeding the cut-off by more than 200 times (up to 160,000 ng/ml).

In general, the immunobioanalytic detection methods, especially the immunochromatographic methods, are subject to the following failures:

1. Failures caused by cross-reactivity and nonspecific binding.
2. Failures by matrix effects.
3. Failures by "anti-animal antibodies".
4. Failures by endogenous components of the sample.
5. Failures by heterophiles and other cross-linking interferers.

(These failures 1-5 could be solved by non-obvious solutions according to the invention).

Of particular interest was the use of a special LowCross Buffer (produced by ScheBo Biotech AG). It includes various detergents, proteins, polyclonal antibodies, surface-active substances as well as substances, which change the surface tension.

All this together with the above-described reagents, substances, etc. of the test kit according to the invention results in an optimum coordination of active pairings in the technical meaning. All this allows the synchronous determination of the two analytes in a combined test cassette.

Surprisingly, it was found that for the solution of the common, synchronous (in the technical meaning) determination of the two analytes on the test strips, the humidity control and the degasification of the liquids when precisely dispensing antibody liquids and colloidal gold was of crucial importance.

Creative, but also systematic working was necessary in order to provide the test kit according to the invention.

Extensive test series were necessary for detecting active pairings and their common, optimum coordination.

This is a basic requirement in order to develop a robust, reproducible and reliable test in the form of a rapid test (platform and/or point-of-care test).

With the extremely large variability of the samples of the available material (stool probands), reagents and antibodies, two pairs each have to be coordinated with each other to obtain step by step reproducible results.

When designing and developing such a complex platform, one comes across numerous physical and chemical phenomena that can affect the test result in an unexpected manner.

Another embodiment of the test kit is the use, after testing "all" optimum, essential active pairings, of the qualitative, semi-quantitative, and quantitative determination of the analytes preferred according to the invention (biomarkers by means of other immunochemical test principles such as ELISA), agglutination, preferably the use of nanoparticles for initiating the agglutination in a liquid phase.

Turbometric, nephelometric measurement technology according to the state of the art allows the generation of measurement data. These measurement data can be processed using appropriate computer software. By means of an "internal" calibration curve (also depending on the batch), for example, a determination of the two analytes according to the invention is possible. Various graphical representations, such as log-log, log-decadic representation, are also possible.

A particular embodiment allows statistical evaluations, e.g., algorithms from the fields of fuzzy logic analyses, classification and pattern and image recognition, explorative data analysis, data visualization, robust and computer-supported statistics, initial data analysis (IDA), and evolving systems (ES), data mining and exploratory data analysis, fuzzy systems, neuronal networks, evolutionary algorithms. Preferred are the algorithms of Prof. Dr. Frank Klawonn. Prof. Klawonn has developed good evaluation strategies that improve data reliability. Prof. Klawonn is the director of the Institute for Applied Computer Science (Institut für angewandte Informatik).

Another embodiment provides an interface to WLAN.

Temporal progresses of patients are also possible.

An individual patient data series is possible for evaluation.

Other apparatus, appliances, etc. for the measurement of the two analytes are conceivable.

Other embodiments platforms "ELISA" are conceivable.

Various arrays: liquid (Luminex) or solid phases (arrays) are possible. All immunochemical detection methods are conceivable.

AGGLUTINATION

Surprisingly, it was found that the droplet size (volume in the nanoliter range) and the distance of these droplets is crucial.

The droplet size and the distance between these droplets is of particular importance. There is thus not dispersed a "line", but individual droplets. The capillary forces of the nitrocellulose membrane absorb droplets in fractions of seconds and cause a line to be formed. The antibodies present in the liquid are distributed in the three-dimensional structure of the nitrocellulose.

Surprisingly, it was found that for achieving a very precise line, the "drying level" is crucial.

Surprisingly, it was also found that the hydrophobicity is very, very important. To ensure that the nitrocellulose membrane to be used is dry, it was previously sealed in aluminum films that are coated on one side and that do not let pass any humidity, opened, provided with antibodies and immediately resealed in the aluminum films plus drying agent. Surprisingly, these production steps were important and were carried out in 6-minutes cycles.

Surprisingly, it was remarkable that in order to ensure a constant flow over the membrane, the construction of the test strip was made in the proper order.

In the reaction zone of the test strip (test result line region), the corresponding lines (pink-red lines) are formed.

The colored test result line (a positive result) is the result of an antigen/antibody reaction, and the determined "Heidelberger curve" shows the measurement signal as a function of antibody excess and antigen excess. It is the aim to use the equivalence range according to the "Heidelberger curve".

The optimum use of the antigen/antibody reaction, i.e., the coordination of the stationary antibodies with the antibody-coupled gold particles present in the liquid phase in the equivalent area of the M2-PK test strip provides an optimum signal for M2-PK on the test strip.

The optimum use of the antigen/antibody reaction, i.e., the coordination of the stationary antibodies with the antibody-coupled gold particles present in the liquid phase in the equivalent area of the Hb test strip provides an optimum signal for Hb on the test strip.

The optimum use of the antigen/antibody reaction, in the equivalent area of the one M2-PK test strip and in the equivalent area of the Hb test strip was the object of the present invention.

The object of the present invention is achieved by the optimum common coordination of active pairings, in particular by the proper choice of the antibodies, the proper choice of detergents, etc., but in particular by the reproducible, high-precision dispensing of the antibody solutions on the two nitrocellulose test membranes.

This allowed the synchronous detection of the two analytes in stool samples from probands. All these active pairings and the technical solutions are described in the application. For this purpose, often non-obvious solutions were needed, lucky coincidences also led to positive results.

The hemoglobin test tube and the M2-PK-tube must be handed over within 48 hours in the physician's office. The dosing tip with the stool sample is transferred into a tube filled with the above-described buffer. Both the tube for the M2-PK test and the tube for the hemoglobin test are vigorously shaken.

The prepared stool sample extracts are applied immediately after each other on the two recesses. After 5-10 minutes, it is read with the aid of the marked line, whether one or both of the measured biomarkers are positive.

Crucial for the reliable determination of a malignant event in the gastrointestinal tract is the choice of so-called "cut-off". The cut-off marks the minimum concentration of the analyte in the sample, indicating a positive result. The cut-off of the hemoglobin test in the test kit according to the invention is between 18 and 38 µg of hemoglobin per gram of stool, preferably 24 µg of hemoglobin per gram of stool. The cut-off for tumor M2-PK is 3-6 units/ml of stool extract, preferably 4±1 units/ml.

The detection limit is 150 ng hemoglobin/ml stool extract.

The evaluation of the test result and the assignment to the risk levels, as shown for example in FIG. 10, can be made manually, semi-automatically or fully automatically. For example, a test cassette according to the invention can be manually loaded to a read-out device, which carries out an evaluation by means of a photocell or camera and then displays the result on a monitor. Preferably, the representation takes place in colors (risk impact scheme). Particular preferred is, for safety reasons, a parallel representation in another form (e.g., risk levels 1-4, or similar).

Of course, the test device may also be configured such that a fully automatic evaluation is possible, e.g., by detection of the gold particles by electro-chemical means or by an optical recording (scanning) of the test kit.

Example 2

The combined rapid test cassette according to the invention does not contain the lateral flow test strip existing on the market to determine the M2-PK, but a novel, improved lateral flow test strip according to the invention for determining the M2-PK (tumor M2-PK plus), e.g. Sartorius.

Furthermore, the combined rapid test cassette does not contain a lateral flow test strip existing on the market for determining hemoglobin, but a novel, improved, lateral flow test strip according to the invention for determining hemoglobin (iFOB plus), e.g. Sartorius.

The invention relates in particular to the combined rapid test and components, as well as all the necessary reagents for synchronously carrying out the immunochromatographic detection method. Synchronously in the linguistic meaning of at the same time, but synchronous also in the technical meaning of the common, optimum coordination of the chromatographic conditions for detecting the two biomarkers M2-PK and hemoglobin in a combined rapid test cassette.

Detection Reagents:

Various detection reagents may be used: latex beads, colloidal gold particles, colloidal silver particles, etc. One of the most important properties of these particles is that the population must be monodisperse with a constant spherical size.

Preferred, according to the invention, are gold particles.

The production of colloidal gold particles is in principle well known. Typically, a solution containing $Au^{3+}$ is chemically reduced under rapid stirring, so that atomic gold particles precipitate, which aggregate in the course of time. Aggregation can be prevented by stabilizing agents. By choosing the right additive, the size of the colloids formed can be set. As an $Au^{3+}$ source, $H[AuCl_4]$ is often used. Sodium citrate solution, sodium borohydride, or hydroquinone can be used as reducing agents. For stabilization, often sulfur compounds (such as alkanethiols) may be used. Solutions containing gold particles are available from various sources.

POLYMER COMPOSITION AND PROTEIN BINDING

For the production of lateral flow tests, nitrocellulose, polyvinylidene fluoride, charge-modified nylon, polyethersulfone are used.

The polymer surface size is dependent on pore size, porosity, thickness, and other structural characteristics.

The surface increases non-linearly with the pore size, but increases linearly with thickness, and non-linearly with porosity. The protein binding to a given surface area depends on the density of the protein, its structure, and its Stokes radius (effective diameter). Furthermore, the binding of the protein to the polymer is dependent on the pH and the immobilization solution.

In the combined rapid test according to the invention, preferably cellulose was used for the so-called sample pad, nitrocellulose for the test membrane, and cellulose for the absorbent pad.

Conjugate/sample pad=22 mm (+/−0.2 mm)×5 mm (+/−0.2 mm).

Nitrocellulose membrane=25 mm (+/−0.2 mm)×5 mm (+/−0.2 mm).

Absorbent pad=16.5 mm (+/−0.2 mm)×5 mm (+/−0.2 mm).

The width of the test membrane=4 mm (+/−0.2 mm).

Capillary flow rate: usually 1-6 cm/min; according to the invention 3.74 cm/min.

DETECTION LIMIT

The particularly preferred cut-off of 4 units M2-PK/ml was found in various studies that investigated the M2-PK stool test ELISA. The chromatographic conditions according to the invention, such as the cutoff value of the combined rapid test according to the invention were determined on the basis of the previously determined cut-off value of the M2-PK stool tests ELISA.

CAPILLARY FLOW RATES FOR NITROCELLULOSE MEMBRANES

The analytical sensitivity decreases with the capillary flow, i.e. the nitrocellulose with the slowest capillary flow time results in the highest analytical sensitivity. Capillary flow times are between 240-75 sec/4 cm. Capillary flow rate according to the invention is 120 sec/4 cm.

List of the Components According to the Invention and of the Active Ingredients According to the Invention

| Component | Reagents | Amount |
| --- | --- | --- |
| Capture line 1. Antibodies 2. Antibodies | Monoclonal anti-mouse anti-M2-PK antibodies mouse anti-hemoglobin antibodies | 0.20-130 µg protein, 0.5-3 µg/cm protein |
| Capture line conjugate | Colloidal gold particles to which anti-M2 antibody and anti-hemoglobin antibodies according to the invention were coupled. | 0.01-0.07 µg protein |
| Control lines antibodies | Special anti-mouse IgG antibodies e.g., such as from the company Jackson Immunochemical (USA). | 0.20-1.30 µg protein 0.05-1 µg/cm protein |

EXTRACTION/RUNNING BUFFER

| Reagents | Amount |
| --- | --- |
| Triton X-100 p.A. | <0.50% |
| Sodium azide | <0.05% |

In the tests during the development of the test kit according to the invention, it has surprisingly been found that both the clinical sensitivity and specificity, but also the chemical-analytical sensitivity are considerably increased when the running liquid in the immunochromatographic test principle has a pH 5-6, preferably a pH of 5.7. This finding is particularly surprising since, according to the state of the art with respect to properties of proteins, these should be present in a partially denatured condition at a pH of 5.7. Therefore, it is surprising that in this area an improvement of sensitivity, specificity, but also of responsiveness is achieved. All immunochromatographic test kits so far available on the market for determining hemoglobin involve a pH from 7 to 7.5 in the running buffer. A final scientific explanation for this cannot yet be given. Possibly, without wishing to be bound to this explanation, there is a partial denaturation in such a way that the epitopes of the analytes are more accessible for the various antibodies. For carrying out this embodiment of the invention with a running liquid having a pH of 5-6, in particular 5.7, a corresponding buffer is needed, namely, an acetate buffer (pH≈5.7), which advantageously further contains 0.1% albumin as a stabilizer. Such buffer systems are familiar to the person skilled in the art, and do not require any further depression at this point.

| 1 | Sample Port |
| --- | --- |
| 2 | Test Line |
| 3 | Control Line |
| 4 | Housing |
| 5 | Sample Pad |
| 6 | Conjugate Pad |
| 7 | Membrane |
| 8 | Absorbent Pad |

Figure 1:
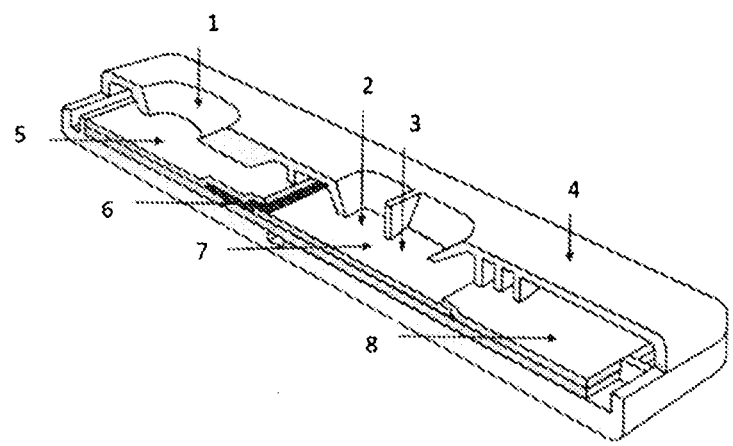
FIG. 1. Schematic view of a test strip in the plastic cassette of a lateral flow rapid test.
Figure 2:
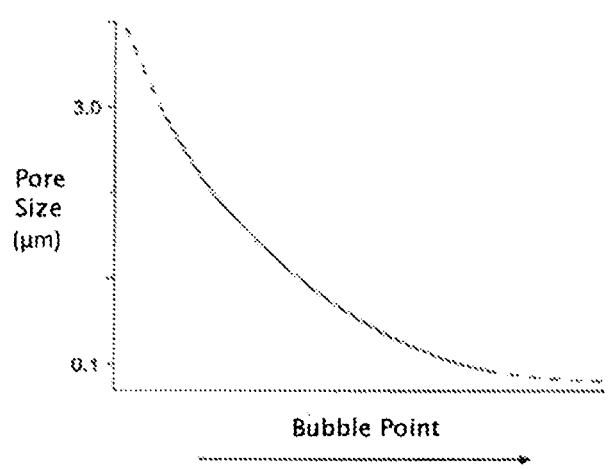

FIG. 2. Relationship between "bubble point" and pore size.

The "bubble point" of the membrane is the pressure required to force the air through a wet membrane.

Figure 3:
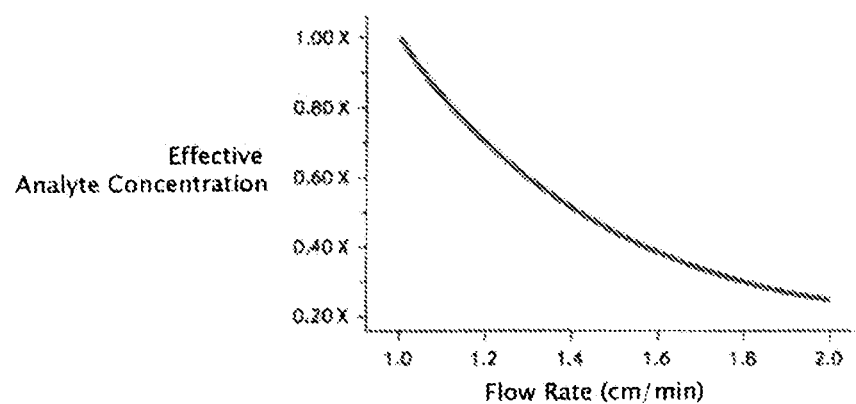

FIG. 3. Effect of capillary flow rate on the analytical sensitivity of a lateral flow rapid test.
Examples:

Flow rate=1.00 cm/min→effective analyte concentration=1.00×.

Flow rate=1.25 cm/min→effective analyte concentration=0.65×.

Figure 4:
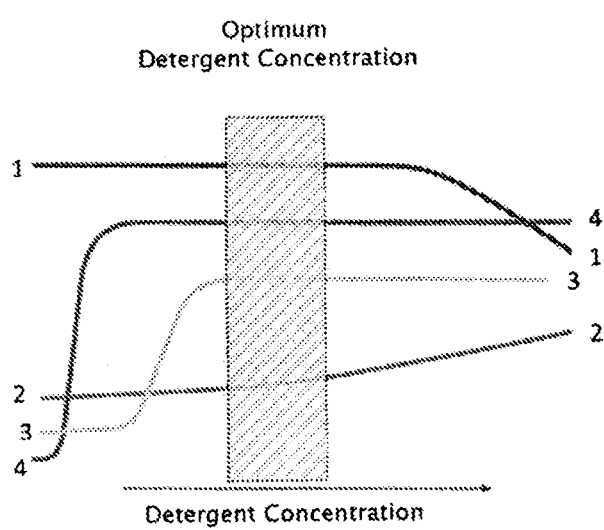

FIG. 4. Effect of a detergent or wetting agent concentration on different performance characteristics of a membrane.

| 1 | Protein Binding |
| --- | --- |
| 2 | Capillary Flow Rate |
| 3 | Strip Consistency |
| 4 | Strip Width |

Figure 5:
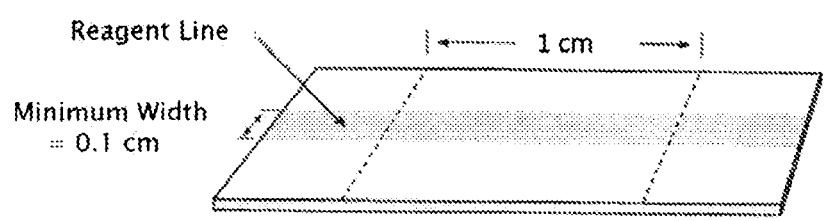

FIG. 5. Calculation of the bandwidth as a function of the distribution rate.

Membrane bed volume=10 µL/cm$^2$.

Reagent dispensing rate=1 µ/cm.

Bandwidth=reagent dispensing rate/membrane bed volume=1 µ/cm/10 µL/cm$^2$=0.1 cm.

Figure 6:
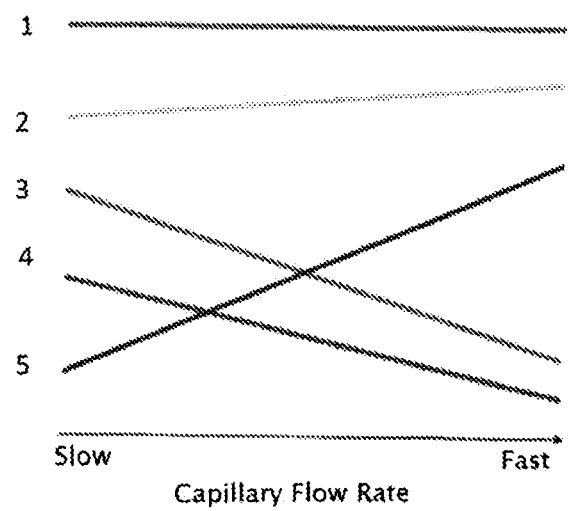

FIG. 6. Typical relationships between flow rate of a membrane and function of an immunochromatographic test.

| 1 | Surface Quality |
| --- | --- |
| 2 | Specificity |
| 3 | Sensitivity |
| 4 | Total Assay Time |
| 5 | Reagent Costs |

Sensitivity=analytical sensitivity=detection in µg=mass.

Figure 7:
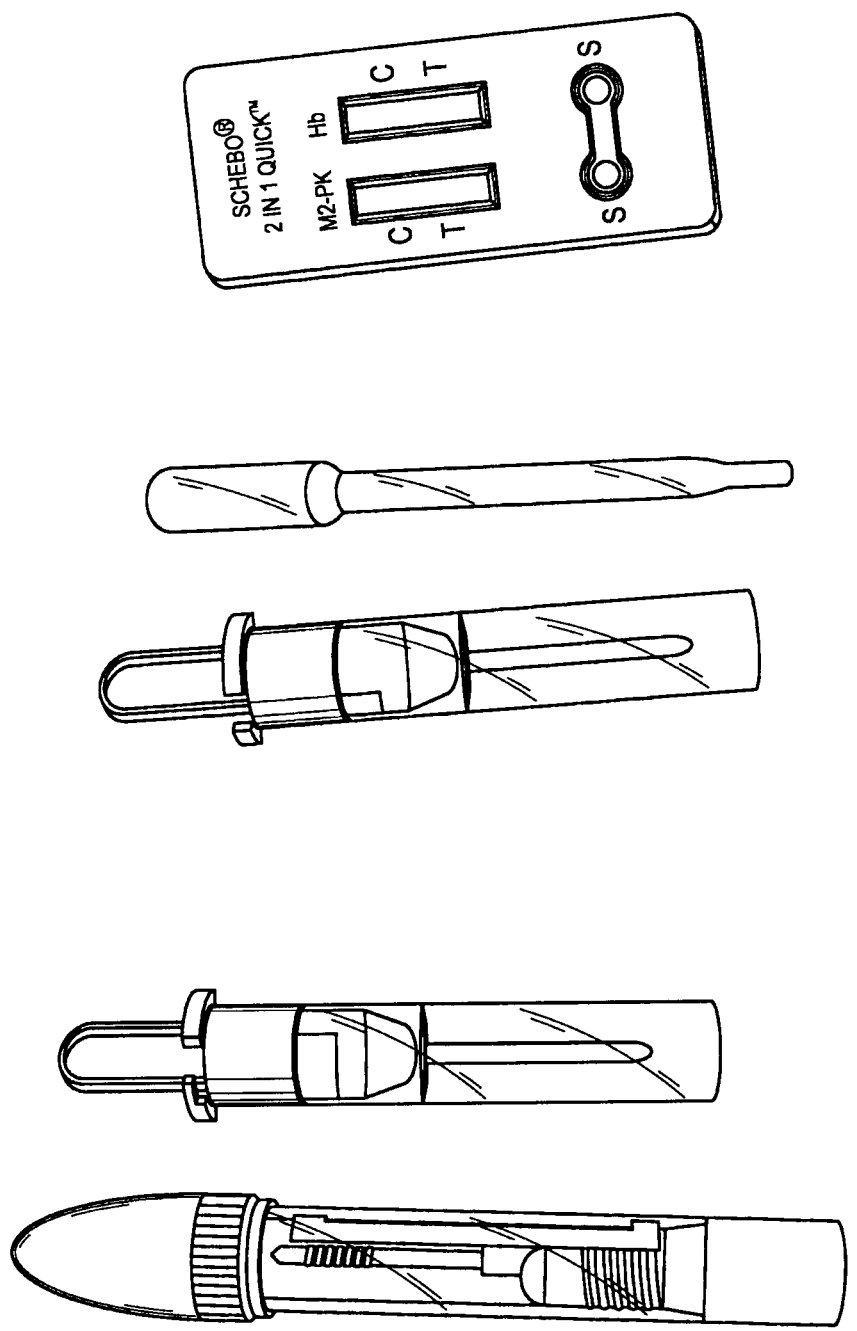
Figure 8:
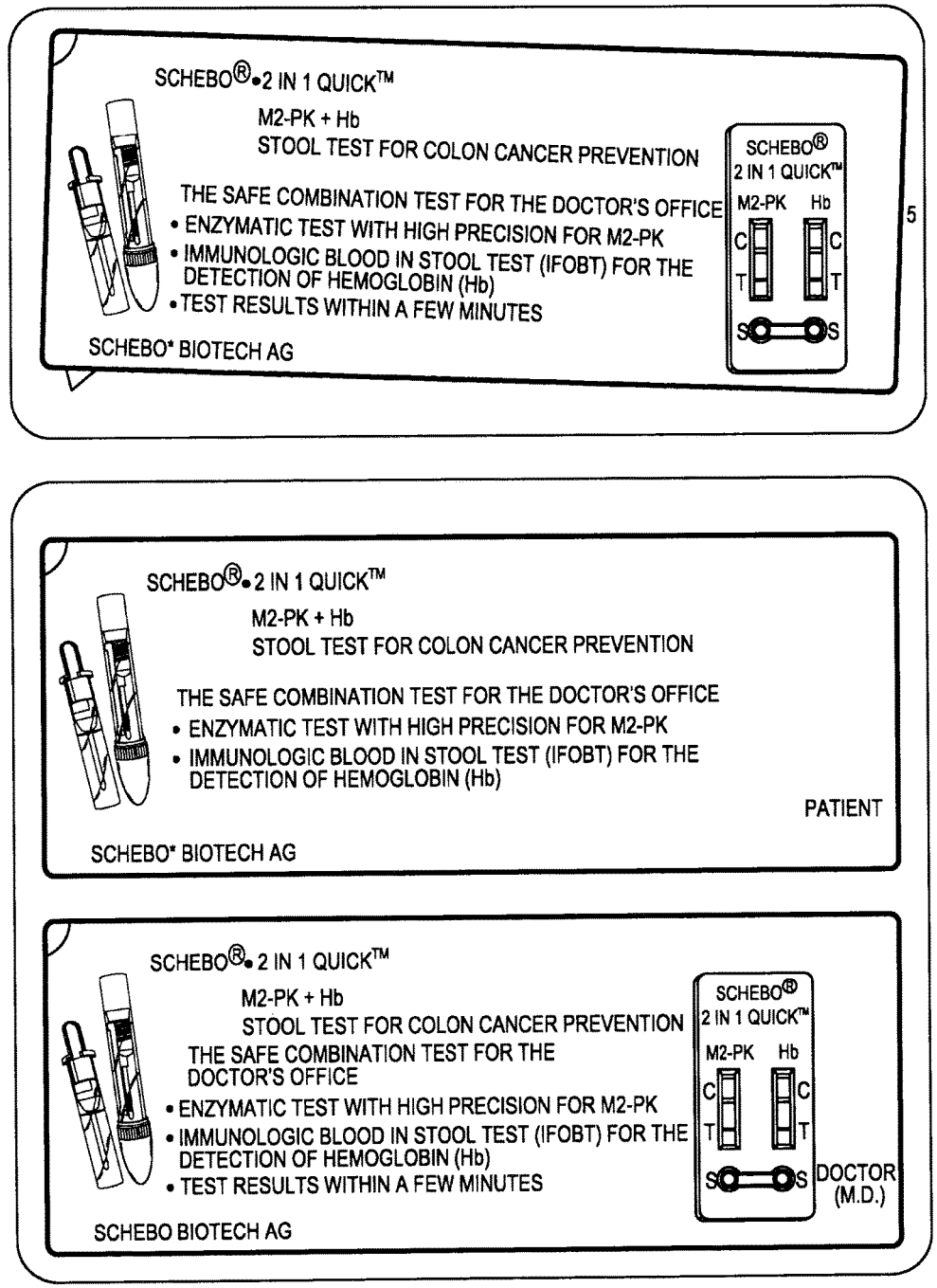
Figure 9:
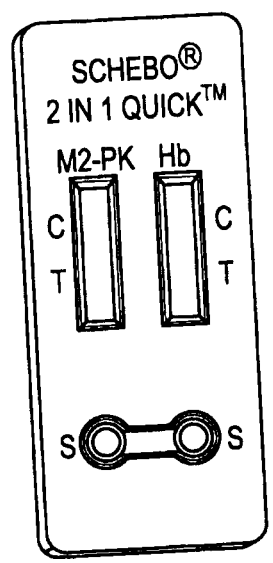

FIGS. 7-9. show in an exemplary way a test kit according to the invention. In FIG. 7 can be seen the sampling devices. FIG. 9 shows the actual test cassette.

FIG. 10. shows an example of the assignment of the various measurement results to risk levels. For ease of reading, the result advantageously is shown in a colored manner. To avoid false readings by, e.g., color-blind persons, additional distinguishing features can be employed (e.g., different shapes, numbers, and/or letters.

OBJECTS OF THE INVENTION

Objects of the invention are therefore:
1. Tool=classifier for diagnosis and assignment in the truth matrix of findings: true and false classifications. Since it is a yes/no question, one can also say the test is positive (means abnormal) or negative (means normal). If the test with only one biomarker is positive, further evaluation of the positive diagnosis is indicated by a colonoscopy.
2. Tool for classifying, based on certain features (determination of M2-PK/hemoglobin).
3. Tool for deciding: should a colonoscopy be performed for further diagnosis: yes/no.
4. Tool for facilitating medical instructions by improved starting diagnosis (significant additional benefits).
5. Tool for facilitating medical decisions on measures, e.g., the application of other diagnostic procedures, e.g., colonoscopy, etc., or therapeutic measures, e.g., surgery, chemotherapy, etc.
6. Tool for improving the prediction accuracy, reporting on the basis of stool samples of probands.
7. Test kit with high overall sensitivity and overall specificity for hemoglobin and M2-PK for detecting colon cancer. The test kit is used as a "dual pre-filter" as part of the colon cancer screening by means of colonoscopy.
8. Test kit with lower "lot-to-lot" deviation that allows for the best possible comparability of test results not only within a production batch but also between batches.
9. Tool for predicting therapeutic success.
10. Tool for improving therapy monitoring.
11. Tool for visualizing the test result (risk impact scheme).
12. The test kit according to the invention is used for predictive problem prevention:
    1. The prevention (Latin: praevenire, avert, prevent) in the sense of keeping undesirable developments from happening.
    a. Prevention of diseases, of pathogenesis, and disease seriousness (severity).
    b. Prevention of certain medical procedures, e.g., unnecessary, dangerous, expensive measures (surgery, chemotherapy, side effects).
    The test kit according to the invention is to be viewed in the context of an optimum damage/benefit/risk consideration, compared to the diagnostic colonoscopy. But also very important is the preservation of quality of life and the prevention of premature death.
13. Object of the test kit according to the invention: The test kit serves for the solution of a serious health problem worldwide. The test kit serves for the "selection" of abnormal probands (increase of efficiency).

This tool is achieved, according to the invention, by providing a combined rapid test.

Combined rapid test for synchronous analytical determination of the enzyme biomarker tumor M2-PK and the biomarker blood (hemoglobin).

Combined rapid test including the test strip (tumor M2-PK plus)+the test strip (iFOB plus) on a test cassette.

Combined rapid test for synchronous analytical determination of the enzyme biomarker tumor M2-PK and the biomarker hemoglobin/haptoglobin complex (Hb/Hp complex).

Combined rapid test including the test strip (tumor M2-PK plus)+the test strip (Hb/Hp complex plus) on a test cassette.

The preferred detection method is the immunochromatographic method. In a particular embodiment, immunochemical methods in array, mini-array format, also turbidimetric methods are further possible. Subject matter of the invention are further monoclonal antibodies.

The use of specific antibodies in the combined rapid test that are specific both in their binding properties for tumor M2-PK or hemoglobin and can be used in immunochromatographic methods (e.g., are "membrane-suitable", "detergent-suitable").

The use of a specific antibody (clone P1F3 AK specifically detects the spatial, dimeric conformation of the M2-PK) for providing the combined rapid test according to the invention. This tumor M2-PK-specific antibody preferably binds to one of the following epitopes or fragments thereof, or combinations (epitopes or fragments thereof) from these which have a minimum length of four amino acids:

| | | | |
|---|---|---|---|
| LAPITSDP | (SeqID 01) | EAEAAIYH | (SeqID 07) |
| VEASFKCC | (SeqID 02) | SGAIIVLT | (SeqID 08) |
| CSGAIIVLT | (SeqID 03) | LQLFEE | (SeqID 09) |
| TEATAVGA | (SeqID 04) | QLFEELRR | (SeqID 10) |
| LRRLAPITSDPTEATA | (SeqID 05) | VEASFKC | (SeqID 11) |
| KCCSGAIIV | (SeqID 06) | KSGRSAHG | (SeqID 12) |

---

The invention claimed is:

1. A test kit for detecting biomarkers in human stool, consisting of
 a first sample tube, having a first stool sampling device,
 a first buffer solution, having buffer 1=10-70 mM phosphate buffer with a pH 6.7 to 7.6 or buffer 2=10-70 mM HEPES buffer with a pH 7.6 to 8.2 or buffer 3=10-70 mM triethanolamine with a pH 7.3 to 7.7 or buffer 4=10-70 mM acetate buffer with a pH 5.7, or mixtures thereof,
 a second sample tube, having a second stool sampling device,
 a second buffer solution, buffer 1=10-70 mM phosphate buffer with a pH 6.7 to 7.6 or buffer 2=10-70 mM HEPES buffer with a pH 7.6 to 8.2 or buffer 3=10-70 mM triethanolamine with a pH 7.3 to 7.7 or buffer 4=10-70 mM acetate buffer with a pH 5.7, or mixtures thereof, a test cassette, having a lateral flow test system with a nitrocellulose membrane as the stationary phase, the nitrocellulose membrane, in turn, having monoclonal tumor M2-PK mouse antibody clone PAT4M3AT, IgG1, and gold-coupled monoclonal mouse antibody clone 1 E3, IgG1, and monoclonal hemoglobin mouse antibody clone M1202100, IgG1, and gold-coupled monoclonal mouse antibody clone HB11-2312, a first opening for applying a stool sample from the first sample tube, a second opening for applying a stool sample from the second sample tube, wherein the analysis result of the first stool sample is positive if the amount of tumor M2-PK is greater than 4±1 units/ml stool extract, and the analysis result of the second stool sample is positive, if the content of hemoglobin exceeds 24 µg hemoglobin per gram of stool.

2. The test kit according to claim 1, wherein the detection of tumor M2-PK and/or hemoglobin is carried out by means of specific monoclonal or polyclonal antibodies, which do not cross-react with other components of the stool.

3. The kit according to claim 1, wherein both buffer solutions include an acetate buffer having a pH of 5-6.

4. The test kit according to claim 1, wherein the determination of hemoglobin of the second stool sample is carried out on the basis of a hemoglobin/haptoglobin complex.

5. The test kit according to claim 1, wherein an antibody is used for determining tumor M2-PK which is selected from the group consisting of monoclonal tumor M2-PK mouse antibody clone PAT4M3AT, IgG1, and gold-coupled monoclonal mouse antibody clone 1 E3, IgG1.

6. The test kit according to claim 1, wherein an antibody is used for determining hemoglobin, which is selected from the group consisting of monoclonal hemoglobin mouse antibody clone M1202100, IgG1, and gold-coupled monoclonal mouse antibody clone HB11-2312.

7. The test kit according to claim 1, wherein a capture antibody is bound to gold colloids.

8. The test kit according to claim 1, wherein a four possible test results are represented by four different colors, letters, numbers, characters, and/or geometric shapes.

9. The test kit according to claim 1, wherein the detection of tumor M2-PK and/or hemoglobin does not cross-react with other pyruvate kinase isoenzymes.

10. The test kit according to claim 1, wherein both buffer solutions include an acetate buffer having a pH of 5.7.

11. The test kit according to claim 9, wherein the isoenzymes are M1-PK, M2-PK in tetrameric form, L-PK, R-PK.

* * * * *